US011123171B2

(12) United States Patent
Forsell

(10) Patent No.: US 11,123,171 B2
(45) Date of Patent: Sep. 21, 2021

(54) FASTENING MEANS FOR IMPLANTABLE MEDICAL CONTROL ASSEMBLY

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/123,583

(22) PCT Filed: Oct. 6, 2009

(86) PCT No.: PCT/SE2009/051108
§ 371 (c)(1),
(2), (4) Date: Apr. 11, 2011

(87) PCT Pub. No.: WO2010/042032
PCT Pub. Date: Apr. 15, 2010

(65) Prior Publication Data
US 2011/0202041 A1 Aug. 18, 2011

Related U.S. Application Data

(60) Provisional application No. 61/227,817, filed on Jul. 23, 2009.

(30) Foreign Application Priority Data

Oct. 10, 2008 (SE) ........................ 0802159

(51) Int. Cl.
*A61F 2/00* (2006.01)
*A61N 1/372* (2006.01)
*A61N 1/375* (2006.01)

(52) U.S. Cl.
CPC ............ *A61F 2/0036* (2013.01); *A61F 2/004* (2013.01); *A61F 2250/0001* (2013.01);
(Continued)

(58) Field of Classification Search
CPC ...... A61F 2250/0001; A61F 2250/0002; A61F 2/0036; A61F 2/004; A61N 1/37288;
(Continued)

(56) References Cited

U.S. PATENT DOCUMENTS 2,060,913 A 11/1936 Weaver
2,795,641 A 6/1957 Rowell
(Continued)

FOREIGN PATENT DOCUMENTS

DE 19511998 10/1996
EP 0102548 3/1984
(Continued)

OTHER PUBLICATIONS

International Search Report for PCT/EP2009/051108, dated Jan. 11, 2010.
(Continued)

*Primary Examiner* — Kami A Bosworth

(57) ABSTRACT

A control assembly for implantation in a patient comprises a first unit adapted for subcutaneous implantation at a first side of a body tissue of said patient, a second unit adapted for implantation in a body cavity of said patient at a second side of said body tissue, wherein at least one of the first and the second unit is adapted to control an implanted powered medical device, and an interconnecting device adapted for mechanical interconnection of the first and second units to keep the assembly in place by the body tissue, the interconnecting device having a cross-sectional area which is smaller than the cross-sectional area of the first unit and the second unit in a plane parallel to the extension of the body tissue.

20 Claims, 15 Drawing Sheets

(52) U.S. Cl.
CPC ... *A61F 2250/0002* (2013.01); *A61N 1/37288* (2013.01); *A61N 1/37518* (2017.08)

(58) Field of Classification Search
CPC .............. A61N 1/375; A61N 1/37518; A61M 5/14276; A61M 2005/14284; A61M 39/0208; A61M 2039/0223; A61M 2039/0261; A61M 2205/3523; A61M 2205/50; A61M 2205/8206
USPC .......................... 604/20, 21, 37, 890.1, 891.1
See application file for complete search history.

(56) References Cited

U.S. PATENT DOCUMENTS

| | | |
|---|---|---|
| 3,209,081 A | 9/1965 | Behrman et al. |
| 3,598,287 A | 8/1971 | De Man |
| 3,662,758 A | 5/1972 | Glover |
| 3,692,027 A | 9/1972 | Ellinwood, Jr. |
| 3,705,575 A | 12/1972 | Edwards |
| 3,731,679 A | 5/1973 | Wilhelmson et al. |
| 3,731,681 A | 5/1973 | Blackshear et al. |
| 3,750,194 A | 8/1973 | Summers |
| 3,817,237 A | 6/1974 | Bolduc |
| 3,855,122 A | 12/1974 | Bourganel |
| 3,863,622 A | 2/1975 | Buuck |
| 3,875,928 A | 4/1975 | Angelchik |
| 3,906,674 A | 9/1975 | Stone |
| 3,923,060 A | 12/1975 | Ellinwood, Jr. |
| 3,954,102 A | 5/1976 | Buuck |
| 4,003,379 A | 1/1977 | Ellinwood, Jr. |
| 4,009,711 A | 3/1977 | Uson |
| 4,019,499 A * | 4/1977 | Fitzgerald ................... 600/30 |
| 4,026,305 A | 5/1977 | Brownlee et al. |
| 4,044,401 A | 8/1977 | Guiset |
| 4,201,202 A | 5/1980 | Finney et al. |
| 4,221,219 A | 9/1980 | Tucker |
| 4,235,222 A | 11/1980 | Ionescu |
| 4,243,306 A | 1/1981 | Bonini |
| 4,246,893 A | 1/1981 | Berson |
| 4,265,241 A | 5/1981 | Portner et al. |
| 4,271,827 A | 6/1981 | Angelchik |
| 4,274,407 A | 6/1981 | Scarlett |
| 4,303,225 A | 12/1981 | Freeman |
| 4,304,225 A | 12/1981 | Freeman |
| 4,318,396 A | 3/1982 | Finney |
| 4,342,308 A | 8/1982 | Trick |
| 4,369,771 A | 1/1983 | Trick |
| 4,400,169 A | 8/1983 | Stephen |
| 4,405,305 A | 9/1983 | Stephen et al. |
| 4,412,530 A | 11/1983 | Burton |
| 4,419,985 A | 12/1983 | Trick |
| 4,424,807 A | 1/1984 | Evans |
| 4,426,893 A | 1/1984 | Miller |
| 4,456,175 A | 6/1984 | Mamrosov et al. |
| 4,464,628 A | 8/1984 | Nozawa |
| 4,491,461 A | 1/1985 | Hoekstra |
| 4,505,710 A | 3/1985 | Collins |
| 4,509,947 A | 4/1985 | Lattin |
| 4,542,753 A | 9/1985 | Brenman et al. |
| 4,550,720 A | 11/1985 | Trick |
| 4,556,050 A | 12/1985 | Hodgson et al. |
| 4,559,033 A * | 12/1985 | Stephen et al. ............... 604/502 |
| 4,559,930 A | 12/1985 | Cobiski |
| 4,559,939 A | 12/1985 | Cobiski |
| 4,563,175 A | 1/1986 | Lafond |
| 4,568,851 A | 2/1986 | Soni et al. |
| 4,578,063 A * | 3/1986 | Inman ............... A61M 39/0247 604/175 |
| 4,583,523 A | 4/1986 | Kleinke et al. |
| 4,584,994 A | 4/1986 | Bamberger et al. |
| 4,587,954 A | 5/1986 | Haber |
| 4,592,339 A | 6/1986 | Kuzmak et al. |
| 4,592,355 A | 6/1986 | Antebi |
| 4,599,081 A | 7/1986 | Cohen |
| 4,602,621 A | 7/1986 | Hakky |
| 4,610,658 A | 9/1986 | Buchwald et al. |
| 4,623,350 A | 11/1986 | Lapeyre et al. |
| 4,628,928 A | 12/1986 | Lowell |
| 4,664,100 A | 5/1987 | Rudloff |
| 4,677,534 A | 6/1987 | Okochi |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,756,949 A | 7/1988 | Spence et al. |
| 4,771,772 A | 9/1988 | DeWitt |
| 4,771,780 A | 9/1988 | Sholder |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,902,279 A | 2/1990 | Schmidtz et al. |
| 4,925,443 A | 5/1990 | Heilman et al. |
| 4,941,461 A | 7/1990 | Fischell |
| 4,942,668 A | 7/1990 | Franklin |
| 4,950,224 A | 8/1990 | Gorsuch et al. |
| 4,958,630 A | 9/1990 | Rosenbluth et al. |
| 4,979,955 A | 12/1990 | Smith |
| 4,982,731 A | 1/1991 | Lue et al. |
| 4,983,177 A | 1/1991 | Wolf |
| 5,006,106 A | 4/1991 | Angelchik |
| 5,012,822 A | 5/1991 | Schwarz |
| 5,042,084 A | 8/1991 | Daly |
| 5,048,511 A | 9/1991 | Rosenbluth et al. |
| 5,057,075 A | 10/1991 | Moncrief et al. |
| 5,062,416 A | 11/1991 | Stucks |
| 5,074,868 A | 12/1991 | Kuzmak |
| 5,098,369 A | 3/1992 | Heilman et al. |
| 5,112,202 A | 5/1992 | Oshima et al. |
| 5,123,428 A | 6/1992 | Schwarz |
| 5,151,082 A | 9/1992 | Gorsuch et al. |
| 5,152,743 A | 10/1992 | Gorsuch et al. |
| 5,160,338 A | 11/1992 | Vincent |
| 5,194,145 A | 3/1993 | Schoendorfer |
| 5,224,926 A | 7/1993 | Gorsuch et al. |
| 5,226,429 A | 7/1993 | Kuzmak |
| 5,250,020 A | 10/1993 | Bley |
| 5,272,664 A | 12/1993 | Alexander |
| 5,297,536 A | 3/1994 | Wilk |
| 5,304,206 A | 4/1994 | Baker, Jr. et al. |
| 5,316,543 A | 5/1994 | Eberbach |
| 5,358,474 A | 10/1994 | Kaldany |
| 5,397,354 A | 3/1995 | Wilk et al. |
| 5,415,660 A | 5/1995 | Campbell et al. |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,501,703 A | 3/1996 | Holsheimer et al. |
| 5,504,700 A | 4/1996 | Insley |
| 5,505,733 A | 4/1996 | Justin et al. |
| 5,509,888 A | 4/1996 | Miller |
| 5,518,499 A | 5/1996 | Aghr |
| 5,518,504 A | 5/1996 | Polyak |
| 5,540,731 A | 7/1996 | Testerman |
| 5,569,187 A | 10/1996 | Kaiser |
| 5,578,069 A | 11/1996 | Miner, II |
| 5,582,580 A | 12/1996 | Buckman, Jr. et al. |
| 5,665,065 A | 9/1997 | Colman et al. |
| 5,676,674 A | 10/1997 | Bolanos et al. |
| 5,690,108 A | 11/1997 | Chakeres |
| 5,702,431 A | 12/1997 | Wang et al. |
| 5,704,893 A | 1/1998 | Timm |
| 5,735,809 A | 4/1998 | Gorsuch |
| 5,735,887 A | 4/1998 | Barreras et al. |
| 5,738,792 A | 4/1998 | Schoendorfer |
| 5,749,909 A | 5/1998 | Schroppel et al. |
| 5,769,877 A | 6/1998 | Barreras |
| 5,771,903 A | 6/1998 | Jakobsson |
| 5,814,020 A | 9/1998 | Gross |
| 5,823,991 A | 10/1998 | Shim |
| 5,827,286 A | 10/1998 | Incavo et al. |
| 5,848,962 A | 12/1998 | Feindt et al. |

(56) References Cited

U.S. PATENT DOCUMENTS

| | | |
|---|---|---|
| 5,858,001 A | 1/1999 | Tsals et al. |
| 5,876,425 A | 3/1999 | Gord et al. |
| 5,900,909 A | 5/1999 | Parulski et al. |
| 5,902,336 A | 5/1999 | Mishkin |
| 5,910,149 A | 6/1999 | Kuzmak |
| 5,928,195 A | 7/1999 | Malamud et al. |
| 5,938,584 A | 8/1999 | Ardito et al. |
| 5,938,669 A | 8/1999 | Klaiber et al. |
| 5,954,715 A | 9/1999 | Harrington et al. |
| 5,964,789 A | 10/1999 | Karsdon |
| 5,978,712 A | 11/1999 | Suda et al. |
| 5,980,478 A | 11/1999 | Gorsuch et al. |
| 5,995,874 A | 11/1999 | Borza |
| 5,997,501 A | 12/1999 | Gross et al. |
| 6,003,736 A | 12/1999 | Ljunggren |
| 6,034,878 A | 3/2000 | Umemura |
| 6,067,474 A * | 5/2000 | Schulman ............ A61N 1/08 607/33 |
| 6,067,991 A | 5/2000 | Forsell |
| 6,074,341 A | 6/2000 | Anderson et al. |
| 6,077,215 A | 6/2000 | Leysieffer |
| 6,095,968 A | 8/2000 | Snyders |
| 6,099,460 A | 8/2000 | Denker |
| 6,102,887 A | 8/2000 | Altman |
| 6,102,922 A | 8/2000 | Jakobsson et al. |
| 6,113,574 A | 9/2000 | Spinello |
| 6,116,193 A | 9/2000 | Goeckner |
| 6,117,067 A | 9/2000 | Gil-Vernet |
| 6,134,470 A | 10/2000 | Hartlaub |
| 6,135,945 A | 10/2000 | Sultan |
| 6,145,505 A | 11/2000 | Nikolchev et al. |
| 6,162,238 A | 12/2000 | Kaplan et al. |
| 6,185,452 B1 | 2/2001 | Schulman et al. |
| 6,197,055 B1 | 3/2001 | Matthews |
| 6,210,347 B1 | 4/2001 | Forsell |
| 6,215,727 B1 | 4/2001 | Parson |
| 6,221,060 B1 | 4/2001 | Willard |
| 6,233,474 B1 | 5/2001 | Lemelson |
| 6,275,737 B1 | 8/2001 | Mann |
| 6,319,191 B1 | 11/2001 | Sayet et al. |
| 6,321,282 B1 | 11/2001 | Horowitz |
| 6,332,466 B1 | 12/2001 | Yoon |
| 6,346,099 B1 | 2/2002 | Altman |
| 6,377,640 B2 | 4/2002 | Trans |
| 6,400,988 B1 | 6/2002 | Gurewitsch |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,456,883 B1 | 9/2002 | Torgerson et al. |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,464,655 B1 | 10/2002 | Shahinpoor |
| 6,470,892 B1 | 10/2002 | Forsell |
| 6,471,635 B1 | 10/2002 | Forsell |
| 6,471,688 B1 | 10/2002 | Harper et al. |
| 6,475,136 B1 | 11/2002 | Forsell |
| 6,480,946 B1 | 11/2002 | Tomishima |
| 6,482,145 B1 | 11/2002 | Forsell |
| 6,502,161 B1 | 12/2002 | Perego et al. |
| 6,503,189 B1 | 1/2003 | Forsell |
| 6,516,282 B2 | 2/2003 | Hedlund |
| 6,571,127 B1 | 5/2003 | Ben-Haim et al. |
| 6,572,585 B2 | 6/2003 | Choi |
| 6,589,229 B1 | 7/2003 | Connelly et al. |
| 6,600,953 B2 | 7/2003 | Flesler et al. |
| 6,638,208 B1 | 10/2003 | Natarajan et al. |
| 6,638,303 B1 | 10/2003 | Campbell |
| 6,640,309 B2 | 10/2003 | Doblar |
| 6,650,943 B1 | 11/2003 | Whitehurst et al. |
| 6,659,936 B1 | 12/2003 | Furness et al. |
| 6,678,561 B2 | 1/2004 | Forsell |
| 6,689,085 B1 | 2/2004 | Rubenstein et al. |
| 6,709,385 B2 | 3/2004 | Forsell |
| 6,740,075 B2 | 5/2004 | Lebel et al. |
| 6,772,011 B2 | 8/2004 | Dolgin |
| 6,839,393 B1 | 1/2005 | Sidiropoulos |
| 6,862,479 B1 | 3/2005 | Whitehurst et al. |
| 6,895,280 B2 | 5/2005 | Meadows et al. |
| 6,911,002 B2 | 6/2005 | Fierro |
| 6,915,165 B2 | 7/2005 | Forsell |
| 6,928,338 B1 | 8/2005 | Buchser et al. |
| 6,929,625 B2 | 8/2005 | Bierman |
| 6,948,918 B2 | 9/2005 | Hansen |
| 6,953,429 B2 | 10/2005 | Forsell |
| 6,954,871 B2 | 10/2005 | Kuhn |
| 6,960,233 B1 | 11/2005 | Berg et al. |
| 6,979,351 B2 | 12/2005 | Forsell et al. |
| 7,003,684 B2 | 2/2006 | Chang |
| 7,011,624 B2 | 3/2006 | Forsell |
| 7,017,583 B2 | 3/2006 | Forsell |
| 7,043,295 B2 | 5/2006 | Starkebaum |
| 7,066,922 B2 | 6/2006 | Angel et al. |
| 7,108,686 B2 | 9/2006 | Burke et al. |
| 7,165,153 B2 | 1/2007 | Vogt |
| 7,207,936 B2 | 4/2007 | Forsell |
| 7,214,233 B2 | 5/2007 | Gannoe et al. |
| 7,217,236 B2 | 5/2007 | Calderon et al. |
| 7,222,224 B2 | 5/2007 | Woo |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,313,639 B2 | 12/2007 | Perego et al. |
| 7,330,753 B2 | 2/2008 | Policker et al. |
| 7,338,437 B2 | 3/2008 | Forsell |
| 7,367,938 B2 | 5/2008 | Forsell |
| 7,371,208 B2 | 5/2008 | Forsell |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,670,280 B2 | 3/2010 | Gloth |
| 7,844,342 B2 | 11/2010 | Dlugos et al. |
| 7,846,160 B2 | 12/2010 | Payne et al. |
| 7,931,582 B2 | 4/2011 | Forsell |
| 7,972,354 B2 | 7/2011 | Prestezog et al. |
| 7,987,853 B2 | 8/2011 | Swann et al. |
| 7,991,476 B2 | 8/2011 | Nachum |
| 8,070,768 B2 | 12/2011 | Kim et al. |
| 8,096,938 B2 | 1/2012 | Forsell |
| 8,096,939 B2 | 1/2012 | Forsell |
| 8,126,558 B2 | 2/2012 | Forsell |
| 8,195,296 B2 | 6/2012 | Longhini et al. |
| 2001/0011543 A1 | 8/2001 | Forsell |
| 2001/0016738 A1 | 8/2001 | Harrington et al. |
| 2001/0041824 A1 | 11/2001 | Zappala |
| 2002/0022759 A1 | 2/2002 | Forsell |
| 2002/0028980 A1 | 3/2002 | Thierfelder et al. |
| 2002/0040208 A1 | 4/2002 | Flaherty et al. |
| 2002/0055711 A1 | 5/2002 | Lavi et al. |
| 2002/0072698 A1 | 6/2002 | Chiang et al. |
| 2002/0072759 A1 | 6/2002 | Fry |
| 2002/0095139 A1 | 7/2002 | Keogh et al. |
| 2002/0095164 A1 | 7/2002 | Andreas et al. |
| 2002/0120219 A1 | 8/2002 | Hovland et al. |
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009201 A1 | 1/2003 | Forsell |
| 2003/0009221 A1 | 1/2003 | Forsell |

(56) References Cited

U.S. PATENT DOCUMENTS

| | | |
|---|---|---|
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0050591 A1 | 3/2003 | McHale |
| 2003/0055442 A1 | 3/2003 | Laufer et al. |
| 2003/0060893 A1 | 3/2003 | Forsell |
| 2003/0066536 A1 | 4/2003 | Forsell |
| 2003/0069547 A1 | 4/2003 | Gonon |
| 2003/0092962 A1 | 4/2003 | Forsell |
| 2003/0088148 A1* | 5/2003 | Forsell ........................... 600/29 |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Forsell |
| 2003/0135090 A1* | 7/2003 | Forsell ................. A61F 2/26 600/38 |
| 2003/0144575 A1 | 7/2003 | Forsell |
| 2003/0144648 A1 | 7/2003 | Forsell |
| 2003/0163029 A1 | 8/2003 | Sonnenschein et al. |
| 2003/0200407 A1 | 10/2003 | Osaka |
| 2003/0208247 A1 | 11/2003 | Spinelli et al. |
| 2003/0231543 A1 | 12/2003 | Matsui |
| 2003/0233143 A1 | 12/2003 | Gharib et al. |
| 2004/0015041 A1 | 1/2004 | Melvin |
| 2004/0024285 A1 | 2/2004 | Muckter |
| 2004/0024419 A1 | 2/2004 | Slepian et al. |
| 2004/0034275 A1 | 2/2004 | Forsell |
| 2004/0068299 A1 | 4/2004 | Laske et al. |
| 2004/0089313 A1 | 5/2004 | Utley et al. |
| 2004/0098113 A1 | 5/2004 | Forsell et al. |
| 2004/0098545 A1 | 5/2004 | Pline et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0162568 A1 | 8/2004 | Saadat et al. |
| 2004/0177918 A1 | 9/2004 | Murata et al. |
| 2004/0230718 A1 | 11/2004 | Polzin et al. |
| 2004/0236877 A1 | 11/2004 | Burton |
| 2004/0249451 A1 | 12/2004 | Lu et al. |
| 2004/0260316 A1 | 12/2004 | Knudson et al. |
| 2005/0009178 A1 | 1/2005 | Yost et al. |
| 2005/0038484 A1 | 2/2005 | Knudson et al. |
| 2005/0055025 A1 | 3/2005 | Zacouto et al. |
| 2005/0060030 A1 | 3/2005 | Lashinski et al. |
| 2005/0075697 A1 | 4/2005 | Olson et al. |
| 2005/0209633 A1 | 9/2005 | Callister et al. |
| 2005/0222678 A1 | 10/2005 | Lashinski et al. |
| 2005/0238506 A1 | 10/2005 | Mescher et al. |
| 2005/0240229 A1 | 10/2005 | Whitehurst et al. |
| 2005/0245957 A1 | 11/2005 | Starkebaum et al. |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2005/0276261 A1 | 12/2005 | Kim |
| 2006/0025855 A1 | 2/2006 | Lashinski et al. |
| 2006/0034358 A1 | 2/2006 | Okamura |
| 2006/0069414 A1 | 3/2006 | Imran et al. |
| 2006/0083899 A1 | 4/2006 | Burazin et al. |
| 2006/0127246 A1 | 6/2006 | Forsell |
| 2006/0129028 A1 | 6/2006 | Krakousky |
| 2006/0142635 A1 | 6/2006 | Forsell |
| 2006/0149124 A1 | 7/2006 | Forsell |
| 2006/0149129 A1 | 7/2006 | Watts et al. |
| 2006/0161217 A1 | 7/2006 | Jaax et al. |
| 2006/0167539 A1 | 7/2006 | Mcewan |
| 2006/0212055 A1 | 9/2006 | Karabey et al. |
| 2006/0224177 A1 | 10/2006 | Finitsis |
| 2006/0229688 A1 | 10/2006 | McClure et al. |
| 2006/0235482 A1 | 10/2006 | Forsell |
| 2006/0247688 A1 | 11/2006 | Olson et al. |
| 2006/0257446 A1 | 11/2006 | Tropsha et al. |
| 2006/0271088 A1 | 11/2006 | Alfrhan |
| 2007/0015959 A1 | 1/2007 | Forsell |
| 2007/0038232 A1 | 2/2007 | Kraemer |
| 2007/0038831 A1 | 2/2007 | Kim |
| 2007/0049790 A1 | 3/2007 | Wagner et al. |
| 2007/0073099 A1 | 3/2007 | Forsell |
| 2007/0092862 A1 | 4/2007 | Gerber |
| 2007/0109019 A1 | 5/2007 | Wu |
| 2007/0121389 A1 | 5/2007 | Wu |
| 2007/0156204 A1 | 7/2007 | Denker et al. |
| 2007/0162670 A1 | 7/2007 | Yang |
| 2007/0167670 A1 | 7/2007 | Coleman et al. |
| 2007/0193632 A1 | 8/2007 | Shu |
| 2007/0204924 A1 | 9/2007 | Delgiacco et al. |
| 2007/0232848 A1 | 10/2007 | Forsell |
| 2007/0250020 A1 | 10/2007 | Kim et al. |
| 2007/0265675 A1 | 11/2007 | Lund et al. |
| 2008/0004487 A1 | 1/2008 | Haverfiled |
| 2008/0045783 A1 | 2/2008 | Forsell |
| 2008/0051718 A1 | 2/2008 | Kavazov et al. |
| 2008/0086179 A1 | 4/2008 | Sharma |
| 2008/0103544 A1 | 5/2008 | Weiner |
| 2008/0139873 A1 | 6/2008 | Peters et al. |
| 2008/0154256 A1 | 6/2008 | Payne et al. |
| 2008/0178889 A1 | 7/2008 | Tal |
| 2008/0200753 A1 | 8/2008 | Forsell |
| 2008/0214888 A1 | 9/2008 | Shalom |
| 2008/0245371 A1 | 10/2008 | Gruber |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0024108 A1 | 1/2009 | Lee-Sepsick et al. |
| 2009/0054725 A1 | 2/2009 | Forsell |
| 2009/0082705 A1 | 3/2009 | Asfora |
| 2009/0131959 A1 | 5/2009 | Rolland |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0145138 A1 | 6/2010 | Forsell |
| 2010/0145139 A1 | 6/2010 | Forsell |
| 2010/0217067 A1 | 8/2010 | Forsell |
| 2010/0286735 A1 | 11/2010 | Garfield et al. |
| 2010/0305656 A1 | 12/2010 | Imran et al. |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |
| 2010/0312164 A1 | 12/2010 | Forsell |
| 2010/0312356 A1 | 12/2010 | Forsell |
| 2010/0318116 A1 | 12/2010 | Forsell |
| 2010/0318117 A1 | 12/2010 | Forsell |
| 2010/0318118 A1 | 12/2010 | Forsell |
| 2010/0324360 A1 | 12/2010 | Forsell |
| 2010/0324361 A1 | 12/2010 | Forsell |
| 2010/0324362 A1 | 12/2010 | Forsell |
| 2010/0324591 A1 | 12/2010 | Forsell |
| 2010/0331614 A1 | 12/2010 | Forsell |
| 2010/0331615 A1 | 12/2010 | Forsell |
| 2010/0331616 A1 | 12/2010 | Forsell |
| 2010/0331617 A1 | 12/2010 | Forsell |
| 2010/0331945 A1 | 12/2010 | Forsell |
| 2010/0332000 A1 | 12/2010 | Forsell |
| 2011/0009894 A1 | 1/2011 | Forsell |
| 2011/0009896 A1 | 1/2011 | Forsell |
| 2011/0009897 A1 | 1/2011 | Forsell |
| 2011/0015473 A1 | 1/2011 | Forsell |
| 2011/0015474 A1 | 1/2011 | Forsell |
| 2011/0040143 A1 | 2/2011 | Forsell |
| 2011/0066254 A1 | 3/2011 | Forsell |
| 2011/0087337 A1 | 4/2011 | Forsell |
| 2011/0172693 A1 | 7/2011 | Forsell |
| 2011/0184230 A1 | 7/2011 | Forsell |

(56) References Cited

U.S. PATENT DOCUMENTS

| | | |
|---|---|---|
| 2011/0192402 A1 | 8/2011 | Forsell |
| 2011/0196192 A1 | 8/2011 | Forsell |
| 2011/0196193 A1 | 8/2011 | Forsell |
| 2011/0196194 A1 | 8/2011 | Forsell |
| 2011/0196271 A1 | 8/2011 | Forsell |
| 2011/0196371 A1 | 8/2011 | Forsell |
| 2011/0196391 A1 | 8/2011 | Forsell |
| 2011/0196411 A1 | 8/2011 | Forsell |
| 2011/0196435 A1 | 8/2011 | Forsell |
| 2011/0196466 A1 | 8/2011 | Forsell |
| 2011/0196476 A1 | 8/2011 | Forsell |
| 2011/0196481 A1 | 8/2011 | Forsell |
| 2011/0196482 A1 | 8/2011 | Forsell |
| 2011/0196483 A1 | 8/2011 | Forsell |
| 2011/0196484 A1 | 8/2011 | Forsell |
| 2011/0196485 A1 | 8/2011 | Forsell |
| 2011/0196486 A1 | 8/2011 | Forsell |
| 2011/0196505 A1 | 8/2011 | Forsell |
| 2011/0196506 A1 | 8/2011 | Forsell |
| 2011/0201870 A1 | 8/2011 | Forsell |
| 2011/0201871 A1 | 8/2011 | Forsell |
| 2011/0201873 A1 | 8/2011 | Forsell |
| 2011/0202041 A1 | 8/2011 | Forsell |
| 2011/0202129 A1 | 8/2011 | Forsell |
| 2011/0202131 A1 | 8/2011 | Forsell |
| 2011/0208231 A1 | 8/2011 | Forsell |
| 2011/0218394 A1 | 9/2011 | Forsell |
| 2011/0224787 A1 | 9/2011 | Forsell |
| 2011/0230930 A1 | 9/2011 | Forsell |
| 2011/0263928 A1 | 10/2011 | Forsell |
| 2012/0029550 A1 | 2/2012 | Forsell |

FOREIGN PATENT DOCUMENTS

| | | |
|---|---|---|
| EP | 01 343 40 | 3/1985 |
| EP | 0 200 286 | 11/1986 |
| EP | 0300552 | 1/1989 |
| EP | 0378251 | 7/1990 |
| EP | 0412191 | 2/1991 |
| EP | 0 583 012 | 2/1994 |
| EP | 0611561 | 9/1994 |
| EP | 0626154 | 11/1994 |
| EP | 0876808 | 11/1998 |
| EP | 1 004 330 | 5/2000 |
| EP | 1 033 142 | 9/2000 |
| EP | 1 072 238 | 1/2001 |
| EP | 1 514 526 | 3/2005 |
| EP | 1563814 | 8/2005 |
| EP | 1563866 | 8/2005 |
| EP | 1563886 | 8/2005 |
| EP | 1 586 283 | 10/2005 |
| EP | 1598030 | 11/2005 |
| EP | 1 681 041 | 7/2006 |
| EP | 1 878 452 | 1/2008 |
| EP | 1 884 259 A1 | 2/2008 |
| EP | 1 913 880 | 4/2008 |
| FR | 2621248 A1 | 7/1989 |
| FR | 2688693 | 9/1993 |
| FR | 2692777 | 12/1993 |
| FR | 27565485 | 6/1998 |
| FR | 2797181 | 2/2001 |
| FR | 2908979 | 5/2008 |
| GB | 8 856 74 | 12/1961 |
| GB | 1194358 | 6/1970 |
| RU | 906-526 | 2/1982 |
| WO | WO 84/01282 | 4/1984 |
| WO | WO 91/00094 | 1/1991 |
| WO | WO 94/27504 | 12/1994 |
| WO | WO 96/01597 | 1/1996 |
| WO | WO 96/11036 | 4/1996 |
| WO | WO 96/39932 | 12/1996 |
| WO | WO 97/41799 | 11/1997 |
| WO | WO 98/50099 | 11/1998 |
| WO | WO 99/18885 | 4/1999 |
| WO | WO 00/09047 | 2/2000 |
| WO | WO 00/09048 | 2/2000 |
| WO | WO 00/15158 | 3/2000 |
| WO | WO 00/16686 | 3/2000 |
| WO | WO 00/33825 | 6/2000 |
| WO | WO 01/12078 | 2/2001 |
| WO | WO 01/12108 | 2/2001 |
| WO | WO 01/45487 | 6/2001 |
| WO | WO 01/45590 | 6/2001 |
| WO | WO 01/47431 | 7/2001 |
| WO | WO 01/47575 | 7/2001 |
| WO | WO 0147434 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | WO 02/38217 | 5/2002 |
| WO | WO 02/40083 | 5/2002 |
| WO | WO 02/053210 | 7/2002 |
| WO | WO 02/058563 | 8/2002 |
| WO | WO 02/087657 | 11/2002 |
| WO | WO 02/100481 | 12/2002 |
| WO | WO 03/002192 | 1/2003 |
| WO | WO 03/033054 | 4/2003 |
| WO | WO 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 98/06358 | 2/2005 |
| WO | WO 2005/072169 | 8/2005 |
| WO | WO 2005/105003 | 11/2005 |
| WO | WO 2006/114004 | 11/2006 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 0147435 | 4/2007 |
| WO | WO 2007/051563 | 5/2007 |
| WO | 2007084042 A1 | 7/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

Written Opinion of the International Searching Authority for PCT/EP2009/051108, dated Jan. 11, 2010.
U.S. Appl. No. 09/373,224, filed Aug. 12, 1999, Forsell.
U.S. Appl. No. 11/988,450, filed May 27, 2009, Forsell.
Webster's II New River side University, 1984, pp. 573,1000.
Anand, Sneh. "Electrical Pacing of the Ampullary Isthmic Junction for Contraception", IEEE Engineering in Medicine & Biology 10th Annual International Conference, 1988.

* cited by examiner

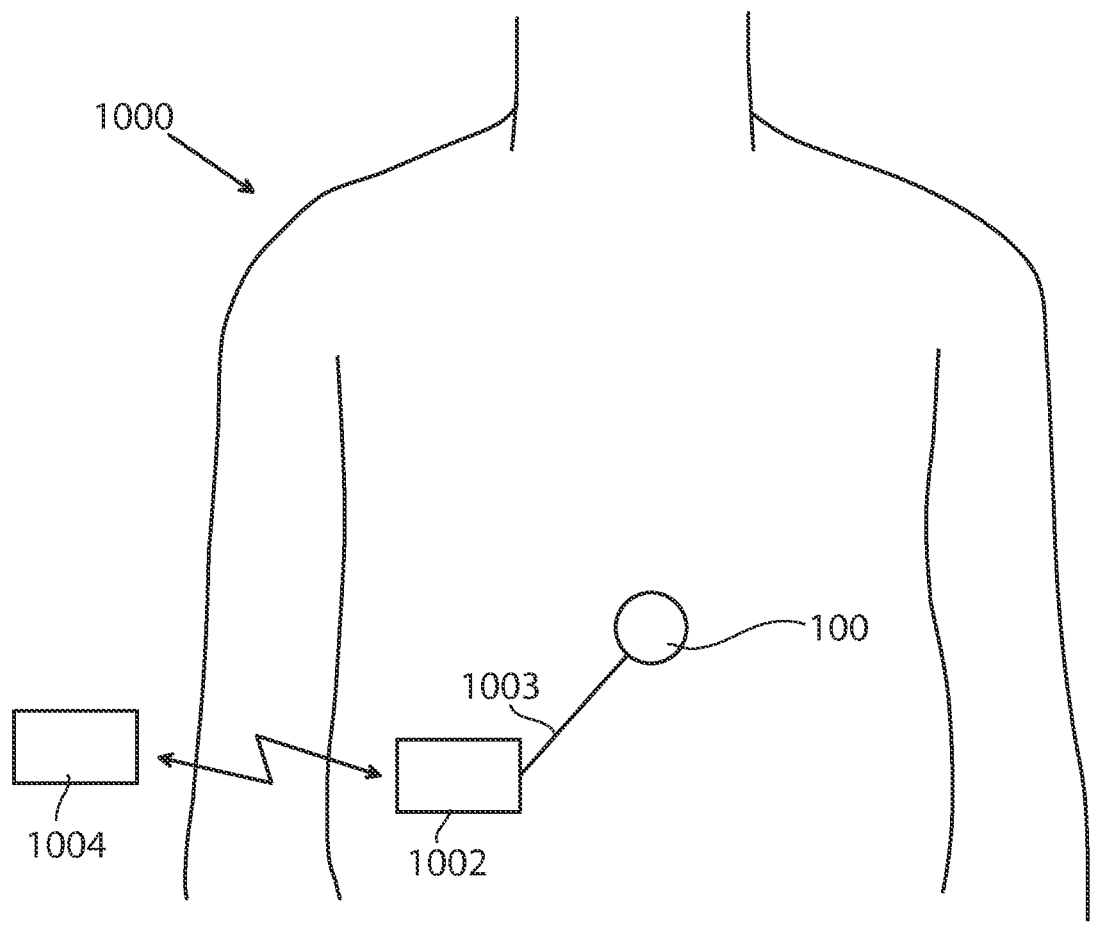

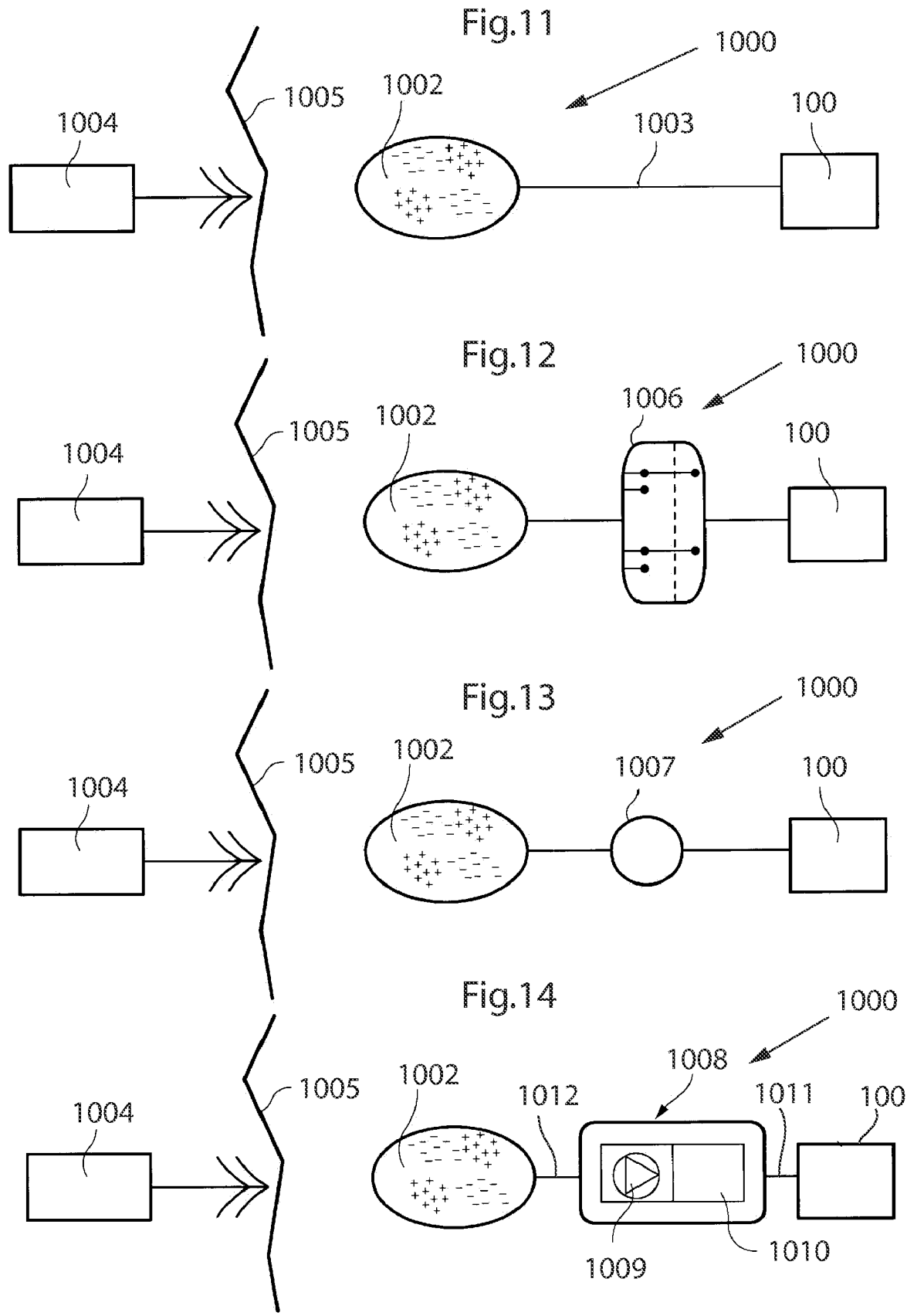

FASTENING MEANS FOR IMPLANTABLE MEDICAL CONTROL ASSEMBLY

This application is the U.S. national phase of International Application No. PCT/SE2009/051108, filed 6 Oct. 2009, which designated the U.S. and claims priority to Swedish Application No. 0802159-4, filed 10 Oct. 2008, and claims the benefit of U.S. Provisional No. 61/227,817, filed 23 Jul. 2009, the entire contents of each of which are hereby incorporated by reference.

FIELD OF INVENTION

The present invention relates generally to a control assembly for implantation in a patient's body and more particularly a control assembly kept in place by a body tissue of the patient. The invention also relates to a system comprising such an assembly and a method of providing a control assembly.

BACKGROUND

Medical devices, designed to be implanted in a patient's body, are typically operated by means of electrical power. Such medical devices include electrical and mechanical stimulators, motors, pumps, etc, which are designed to support or stimulate various body functions. Electrical power can be supplied to such an implanted medical device from a likewise implanted battery or from an external energy source that can supply any needed amount of electrical power intermittently or continuously without requiring repeated surgical operations.

An external energy source can transfer wireless energy to an implanted internal energy receiver located inside the patient and connected to the medical device for supplying received energy thereto. So-called TET (Transcutaneous Energy Transfer) devices are known that can transfer wireless energy in this manner. Thereby, no leads or the like penetrating the skin need to be used for connecting the medical device to an external energy source, such as a battery. A TET device typically comprises an external energy source including a primary coil adapted to inductively transfer any amount of wireless energy, by inducing voltage in a secondary coil of an internal energy receiver which is implanted preferably just beneath the skin of a patient.

Another example of an implanted device required for the operation of an implanted medical device is a subcutaneous injection port adapted for receiving an injection needle or the like for injection and/or refraction of a fluid to/from the medical implant.

An implanted energy receiver or other implanted devices required for the operation of an implanted medical device must in some way be located in the patient's body in a secure and convenient way. It is often the case that the implanted device must be located close to the patient's skin in order to keep the distance between an external device, such as an energy transmitter, and the implanted device to a minimum. In practice, this means subcutaneous placement of the implanted device.

It is also often important that the implanted device is kept in a relatively fixed position so that for example energy transfer can be performed accurately.

EP 0 134 340 A1 describes a peritoneal injection catheter apparatus comprising a receiving reservoir interconnected with the peritoneal cavity by a hollow stem provided with flanges. The apparatus is secured in place by means of sutures and the flanges are only provided to minimize the likelihood of catheter obstruction during use by a patient.

SUMMARY OF THE INVENTION

According to the present invention a control assembly is provided, which is suited for subcutaneous placement and which is kept in a relatively fixed position.

The invention is based on the realization that the control assembly can be provided in two parts on different sides of a body tissue of the patient and be kept in place by an interconnecting device.

Thus, a control assembly according to the invention for implantation in a patient comprises a first unit adapted for subcutaneous implantation at a first side of a body tissue of said patient, a second unit adapted for implantation in a body cavity of said patient at a second side of said body tissue, wherein at least one of the first and the second unit is adapted to control a powered medical device, and an interconnecting device adapted for mechanical interconnection of the first and second units to keep the assembly in place by the body tissue, the interconnecting device having a cross-sectional area which is smaller than the cross-sectional area of the first unit and the second unit in a plane parallel to the extension of the body tissue.

In a preferred embodiment, the control assembly comprises an energy receiver. It is preferred that the energy receiver is adapted to receive wireless energy. The energy receiver may be a coil, which may be adapted to be used as an antenna.

In one embodiment, the control assembly comprises a pump.

In another embodiment, the control assembly comprises a battery.

In one embodiment, the interconnections device is elastic to handle movements of the patient.

The control assembly may comprise at least one of the following parts: pump, motor, electronic circuit, power circuit, control circuit, sensor, temperature sensor, feed back receiver, feed back transmitter, capacitor, rechargeable battery, wireless energy receiver, pressure sensor, reservoir, hydraulic fluid, gear box, servo and reversed servo, or any combination thereof. Thus, by providing first and second interconnected units, the control assembly can be easily adapted to different applications.

Each part is provided in one or more pieces.

The different parts of the control assembly may all be positioned either in the inner or outer part of the control assembly independent of each other or in both the inner and outer part. In one embodiment, the energy receiver comprises a coil, which preferably is provided in the first unit adapted to be subcutaneously implanted between the skin of the patient and the body tissue. The first unit with the coil can then be made thin, which is suitable for subcutaneous placement, while the coil can be connected to for example an electronic circuit provided in the second unit. The coil can also be used as an antenna, functioning as a receiver and transmitter of data to and from a control unit.

The control assembly may be part of a system. The system may be hydraulically, mechanically, or pneumatically operated. By providing a control assembly which is connected to an implanted medical device, different control configurations can be easily obtained.

According to one aspect, a method for placing a control assembly is provided. By having a control assembly with first and second units and an interconnecting device, the implantation of the control assembly is easy to perform, since each unit is smaller than the assembled control assembly.

Further preferred embodiments are defined by the dependent claims.

BRIEF DESCRIPTION OF DRAWINGS

The invention is now described, by way of example, with reference to the accompanying drawings, in which:

FIG. 10 illustrates a system for treating a disease, wherein the system includes an implanted assembly of the invention implanted in a patient.

FIGS. 11-25 schematically show various embodiments of the system for wirelessly powering the implanted assembly shown in FIG. 1.

FIGS. 30-46 show various ways of arranging hydraulic or pneumatic powering of an implanted assembly implanted in a patient.

DETAILED DESCRIPTION OF PREFERRED EMBODIMENTS

Figure 1:
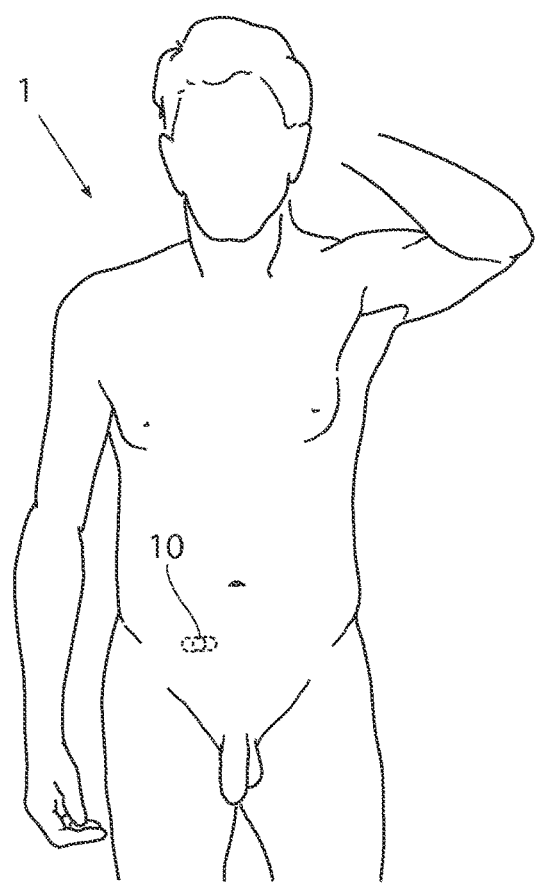
FIG. 1 is an overall view of a human patient's body showing the position of an implanted assembly according to the invention.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

The term "functional parts" is to be interpreted as all parts of the control assembly for the electrical or hydraulic operation of the assembly.

FIG. 1 shows the body of a human patient 1. A control assembly 10 adapted for controlling an implanted medical device is shown subcutaneously implanted in the abdominal area of the patient's body. Although a specific position for the control assembly is shown in the figure, it will be appreciated that the control assembly can be provided essentially anywhere in the patient's body, preferably relatively close to the implanted medical device which it is adapted to control. Generally speaking, the control assembly 10 may be placed in the abdomen, thorax, muscle fascia (e.g. in the abdominal wall), subcutaneously, or at any other suitable location.

Figure 2:
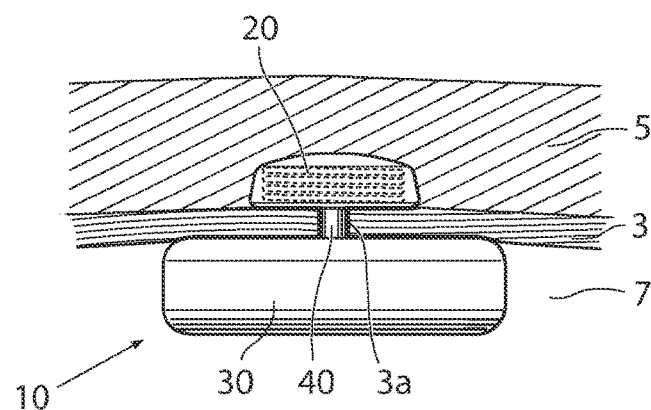
FIG. 2 is a side view of a first embodiment of an implanted assembly according to the invention mounted to a body tissue.

An overall side view of the control assembly 10 is shown in FIG. 2. The control assembly comprises a first unit 20 subcutaneously implanted at a first side of a body tissue 3 in the patient, such as the rectus abdominis muscle running vertically on each side of the anterior wall of the human abdomen. In other words, the first unit is positioned between the skin 5 of the patient and the body tissue 3.

A second unit 30 is implanted in a body cavity 7 of the patient at a second side of the body tissue 3, i.e., that the side opposite of the side at which the first unit 20 is provided.

Figure 3:
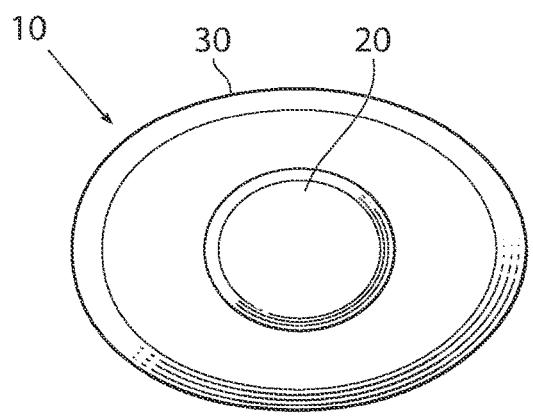
FIG. 3a is a top view of the assembly shown in FIG. 2 having elliptical shape.
FIG. 3b is a top view of the assembly shown in FIG. 2 having circular shape.
FIG. 3c is a sectional view of the assembly shown in FIG. 2 provided with a resilient cover.
Figure 3:
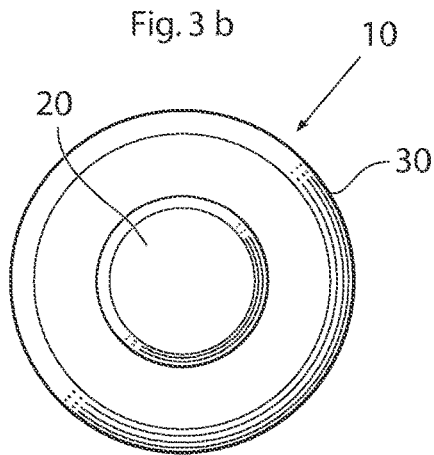
Figure 3:
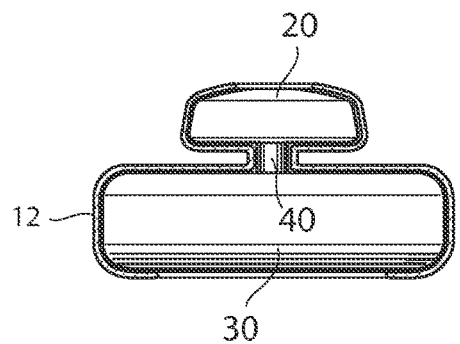

The first and/or second units 20, 30 preferably have circular or elliptical cross-sectional shape when viewed from outside the patient's body, see FIGS. 3a, 3b, showing a top view of the assembly having elliptical and circular shape, respectively. Combined with a smoothly curved sectional shape, this avoids any sharp corners on the units 20, 30, which could cause injuries to the patient in which the control assembly 10 is implanted.

The first and second units 20, 30 may be covered by a cover 12 made of for example silicone or another material providing protection. The cover 12, which preferably is resilient so as to follow the contours of the first and second units, also seals the control assembly 10, thereby protecting electronics and other sensitive components of the control assembly.

If a cover encloses the first and second units 20, 30, these will be kept together mechanically, thereby assisting the interconnecting device 40 in its interconnecting function.

An interconnecting device 40 constitutes a mechanical interconnection between the first and second units 20, 30 so that the control assembly 10 is kept in place by the body tissue 3. The interconnecting device has a cross-sectional area which is smaller than the cross-sectional area of the first unit and the second unit in a plane parallel to the extension of the body tissue. In this way, a hole 3a in the body tissue 3 through which the interconnecting device 40 extends can be sufficiently small so that it is avoided that one or the other of the units 20, 30 "slips through" the body tissue 3. Also, the cross-sectional shape of the interconnecting device 40 is preferably circular so as to avoid damage to the body tissue 3.

The interconnecting device 40 can be integral with one of the first and second units 20, 30. Alternatively, the interconnecting device 40 is a separate part, which is connected to the first and second units 20, 30 during implantation of the control assembly 10.

In a preferred embodiment, the interconnecting device 40 is hollow so as to house various wires, hoses etc. electrically or hydraulically interconnecting the first and second units 20, 30.

Alternatively or additionally, the interconnecting device 40 is made of an elastic material, such as rubber, so that the control assembly 10 can adapt to the movements of the patient in which it is implanted.

Figure 4:
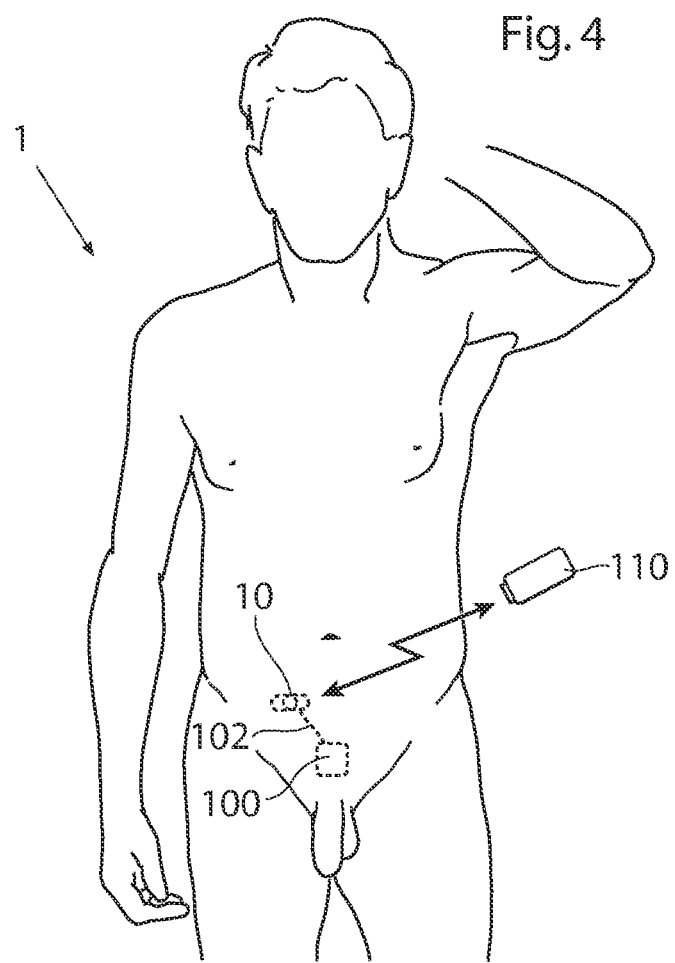
FIG. 4 is an overall view of a human patient's body showing an implanted assembly according to the invention connected to an implanted medical device.

The control assembly 10 is adapted to control a powered implanted medical device 100, see FIG. 4. The implanted medical device can be any kind of powered operation device, such as a hydraulically, pneumatically or mechanically powered operation device. The medical device 100 can be any kind of implant, such as a constriction device adapted to constrict and release a bodily lumen or vessel, a stimulation device adapted to electrically stimulate a bodily organ, an inflatable device adapted to fill for example the corpora cavernosa of the patient etc. The implanted medical device is preferably very small, having a diameter of less than 5 centimeters, to fit in the different target areas of the body.

Depending of the kind of power required to control the medical device 100, an interconnection 102 in the form of an electrical wire, a pneumatic hose etc., is provided between the control assembly 10 and the medical device 100.

The control assembly 10 is adapted to receive energy, preferably wireless energy, transmitted from an external energy source or energizer 110 located outside the skin in the vicinity of the control assembly 10. The energizer 110, which is an external device which functions as the charging equipment and control device for the control assembly, is connected via a connection, such as a serial RS232 connection, to a computer 112, such as a standard desktop PC or a laptop computer. The PC software implements the user interface to the implant system, and function as the control unit and read back unit of the implant system.

Figure 5:
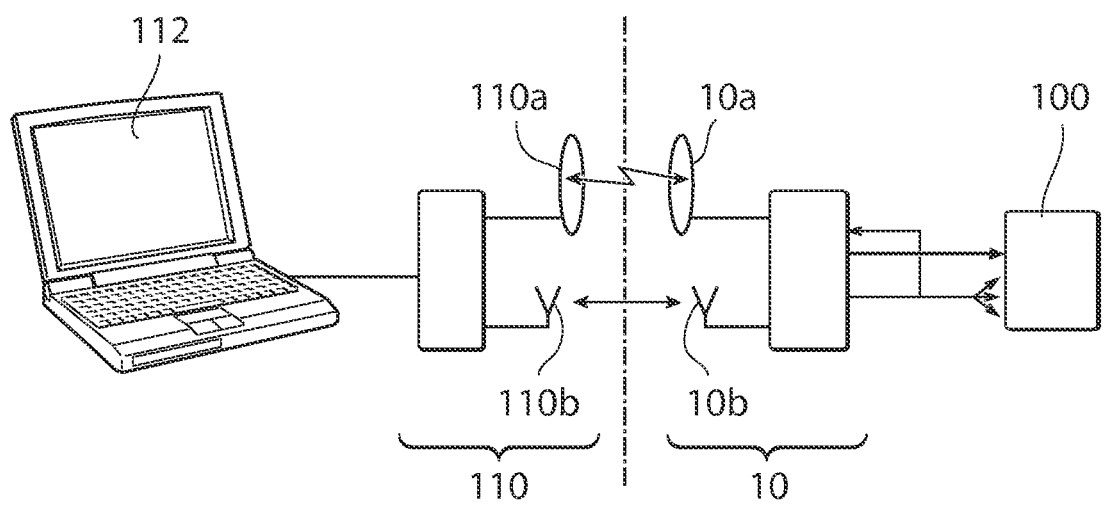
FIG. 5 is a block diagram of a control system comprising a control assembly according to the invention.

A block diagram of the implant system is shown in FIG. 5. Energy is transferred by means of the wireless coupling between an energizer coil 110a forming part of the energizer 110 and a control assembly coil 10a forming part of the control assembly 10. Similarly, control information is transferred between the energizer 110 by means of a wireless communications interface comprising an energizer antenna 110b forming part of the energizer 110 and a control assembly antenna 10b forming part of the control assembly 10. In this way, both energy and communication information can be transferred wirelessly to and from the control assembly 10.

Although separate devices are shown for transfer of energy and information, i.e., the coils and the antennas, respectively, it will be appreciated that the coils 10a, 100a can be implemented for use as an antenna as well, whereby control information can be transferred by means of the coils and no separate antennas are needed for that purpose.

The functional parts of the control assembly 10 can be provided either in the first unit 20 or in the second unit 30 or in both the first and the second unit. In other words, at least one of the first and the second unit is adapted to control a powered implanted medical device.

Figure 6:
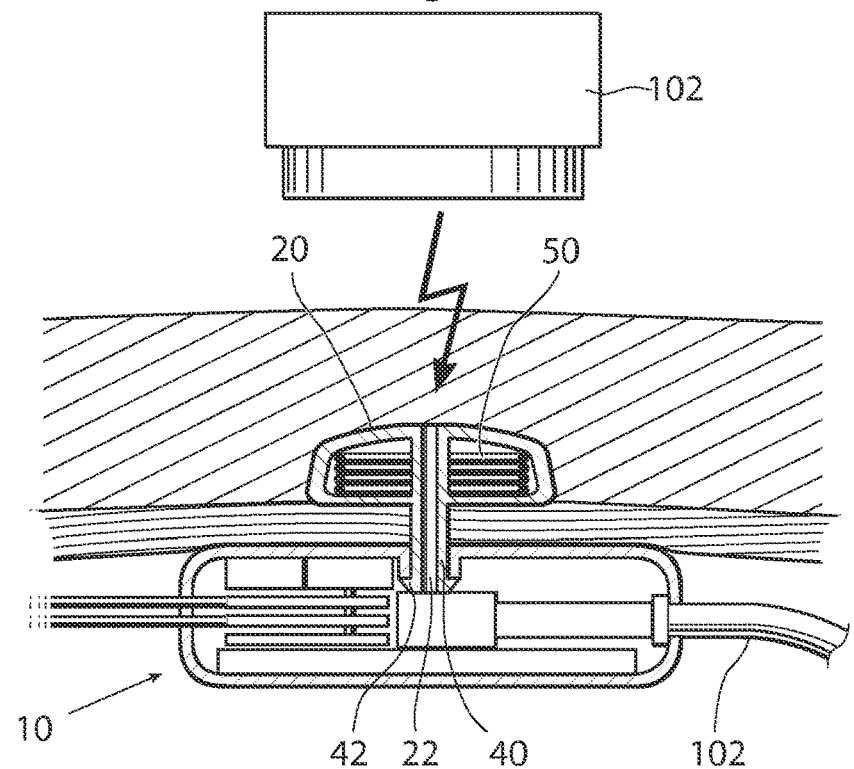
FIG. 6 is a sectional view of the control assembly shown in FIG. 2.

FIG. 6 is a sectional view of the control assembly 10 showing an example of the contents of the first unit 20, the second unit 30 and the interconnecting device 40. It is also shown that the interconnecting device 40 is provided integral with the first unit 20, forming an extension from the central portion of the first unit. The outer end of the extension is provided with barbs 42 engaging the rim of a hole 22 provided in the central portion of the second unit. In this way, the control assembly 10 can be assembled by a simple snap-together operation, as will be described in more detail below.

Coil 50

Figure 7:
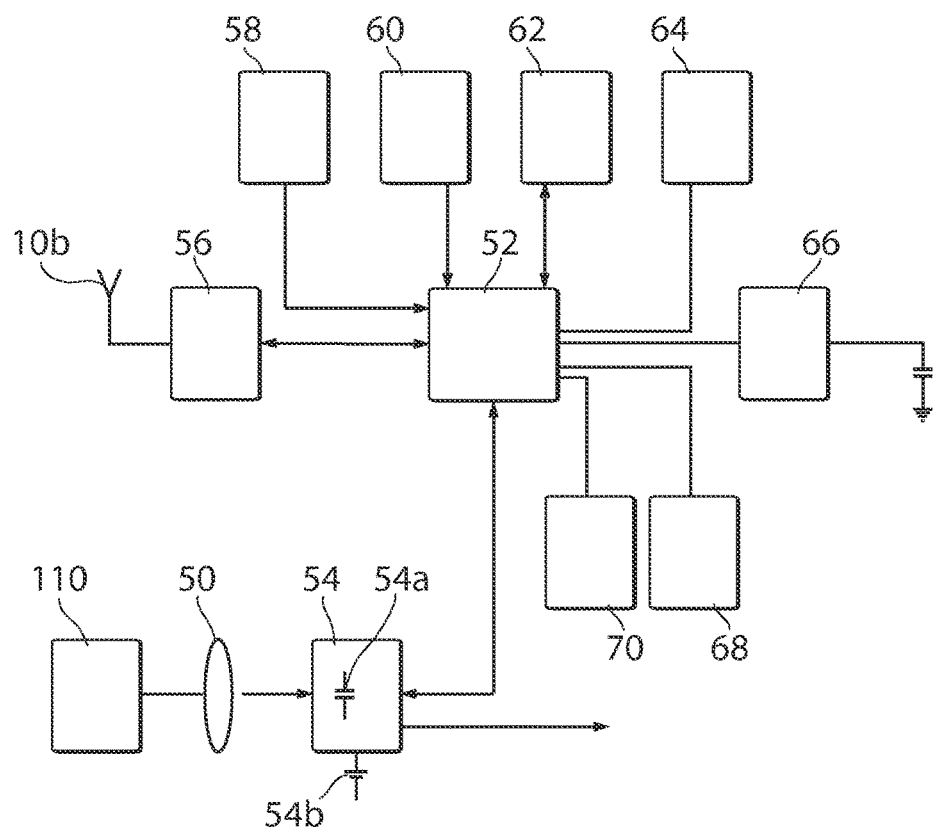
FIG. 7 is a block diagram showing the different parts of a control assembly according to the invention.

A coil 50 is provided in the first unit, the coil being an energy transfer coil arranged to pick up wireless electromagnetic energy and signals from an external unit. The number of rounds in the coil is adapted for the specific operation and is preferably at least ten. The end portions of the coil 50 extend perpendicularly to the general extension of the coil and are lead through the hollow interconnecting device 40 to be connected to the functional parts provided in the second unit 30, shown as a block diagram in FIG. 7. The functional parts shown in this figure is a non-limiting example of the different parts comprised in a control assembly according to the invention.

MCU 52

A micro controller unit (MCU) 52 is provided as a main controller unit of the control assembly 10 and it thus provided with control software for controlling the operation of the functional parts of the control assembly. In a preferred embodiment, this MCU is a Texas Instruments MSP430F149 MCU. Although not shown in the figure, the MCU can be supplemented by additional peripheral circuits, such as a gate array implemented as an application specific integrated circuit (ASIC), acting as an interface to the various functional parts.

The MCU 52 receives commands from the energizer 110 via a wireless communication link, see below, and makes decisions about actions. The MCU 52 thus supervises all functions in the control assembly 10.

The MCU stores application specific parameters and calibration data in an external EEPROM (not shown).

The main functionality of the control assembly 10 is that all operations, such as stimuli, adjustments or measurements are initiated via the energizer 110. Thus, the energizer has two main functions: User interface via RF communication with the control assembly 10 and energy transfer to the control assembly.

The control assembly 10 can be OFF or in Standby when "unconnected". All functions within the control assembly are controlled via the wireless communication link.

The energy transfer function runs in the background as soon as the user has initiated a charge operation. The coupling between the energizer and the receiver coil is displayed by means of a graphical user interface (GUI) on the display of the energizer 110.

If the communication is interrupted during operation, the active function is terminated with a warning message. As soon as correct connection is obtained the last function can be re-activated from the GUI.

Charge Control Unit 54

The MCU 52 is connected to a charge control unit 54, which in turn is connected to the coil 50, which in this embodiment is provided in the first unit 20. The charge control unit comprises an energy storage capacitor 54a, from which the normal power supply is taken. In the preferred embodiment, the energy storage capacitor 54a has a value of at least 300 Farad with a maximum voltage of 2.3V. The energy storage capacitor is normally connected to the energy transfer coil 50, preventing hazardous voltages to occur at the supply circuits. The voltage from the energy transfer coil 50 is rectified by means of half-wave rectification.

The transferred energy is set by the voltage on the energizer transmit coil 110a, see FIG. 5, and the geometric placement relative the energy transfer coil 10a on the control assembly. The leakage inductances make the behavior of a current generator, that is, the voltage across the energy storage capacitor 54a will have a very little influence on the current.

The charge function is controlled from the energizer software, which depends on current and voltage readings on the reservoir capacitor.

The applied energy transfer will charge the capacitor up to a limit voltage, which in the preferred embodiment is 2.3V, while the charge current preferably is limited to 2 A by the energizer design. If the energy storage capacitor energy drops below a lower limit voltage, in the preferred embodiment 1.2V, MCU 52 will be notified to terminate any activity and go to STAND-BY mode.

An over voltage protection will disconnect the receiver inductor if the energy storage capacitor voltage reaches 2.35V. All functional parts of the control assembly will still be supplied from the capacitor and a battery charge process will continue.

Thus, the voltage will vary between 1.0 and 2.3V dependent of the charge status. This voltage feeds a switch converter for supplying the MCU including any gate array. It is preferred that the gate array supply may be shut down by the MCU to save energy.

The control assembly shall be functional for 36 hours relying on the capacitor only.

A chargeable battery 54b is also provided as part of the charge control unit 54. The capacity of the battery is preferably approximately ten times that of the energy storage capacitor 54a. In the preferred embodiment, the battery used is three 1.2 V batteries, such as Varta V500-HT, connected in series. This gives a nominal voltage of 3.6V. The battery management consists of two main activities: Charging and discharging (transfer energy to the reservoir capacitor). Normally the battery is unused and energy is supplied from the capacitor.

A battery charging functionality is implemented in hardware with supervision and control from the MCU 52. The chargeable battery is charged from the energy storage capacitor 54a when the voltage across the energy storage capacitor exceeds 1.9V. This limit will prevent the battery charger from emptying the capacitor energy. When the voltage across the energy storage capacitor is less than 1.3V, the battery will charge the energy storage capacitor a constant current by means of a step-down converter (not shown). The charge current is in the preferred embodiment 350 mA with dv/dt detection.

Temperature supervision will turn off any charge operation if the battery temperature increases more than 0.7° C. per min.

The energy transfer is controlled from the software in the computer 112. The MCU 52 will read the voltage and current on the energy storage capacitor 54a. The values are then on command transmitted to the computer 112, which controls the energizer. If the energy storage capacitor 54a has a 300 F capacitance and the charge current is normally well below 2 A, the voltage changes will be very slow—minutes for a 0.1 V increase. This slow behavior makes an ordinary PI-regulator superfluous. The preferred embodiment is an on/off regulator with a 100 mV hysteresis gap.

At the very startup when there may be no energy in the capacitor. A special bypass power will turn on the MCU/transceiver. Thus the feedback communication system will be active almost immediately when the energizer coil is applied.

Power Modes

The control assembly 10 can be in four different power modes, namely:

OFF: All circuits are turned off. The transceiver 56 is powered from the chargeable battery 54b, but in sleep mode.

WAKE-UP: The power is fed from the energy transfer coil 50, unconditionally of the status of the energy storage capacitor 54a or the chargeable battery 54b. This makes the control assembly to respond immediately when the energizer is applied.

STAND-BY: MCU active but no stimuli, sensor or motor voltage active.

ACTIVE: The MCU in operation. Motor/Sensors/Stimuli etc. active

The mode is controlled by the software in the MCU.

Transceiver 56

The MCU 52 communicates with the energizer by means of the antenna 10b, see FIG. 5, which is electrically connected to a transceiver 56 in the control assembly 10. The transceiver 56 is in turn connected to the MCU 52. The transceiver 56 can be any suitable transceiver circuit and is in the described embodiment a circuit marketed under the name ZL70101 by Zarlink Semiconductor Inc. This provides RF communication using the MICS standard. The transceiver preferably uses a serial peripheral interface (SPI) to communicate with the MCU and is specified for 2.1-3.6V supply. The transceiver needs to be under continuous power but have a low power mode with very low quiescent current where it can be woken up by using either by toggling a wakeup input or alternatively by MICS band or 2.4 GHz radio signals.

Antenna 10b

In the preferred embodiment, the antenna 10b is adapted to support MICS telemetry that operates in the dedicated 402-405 MHz band. The most probable implementation of the transceiver 56 will use a system that can be implemented using also a secondary 2.4 GHz ISM band for wake up purposes, which will then also require attention to safeguard antenna functionality also at these frequencies. The wake up antenna is assumed to be identical to the MICS antenna since alternate solutions would require separate hermetic feedthrough connections that adds considerable costs. The 2.4 GHz aspect of the antenna is an electrically large antenna that works well with most MICS antenna implementations.

Temperature Sensor(s) 58

One temperature sensor will be use for sensing the temperature of the battery and one sensing the encapsulation. It is also possible to connect one or more external temperature sensors. The sensor accuracy is typically +/−0.5 degrees between −30-+70 degrees and better than +/−0.25 degrees between 20-45 degrees.

Pressure Sensors(s) 60

One or more pressure sensors 60 are connected to an A/D input of the MCU 52. The pressure sensors preferably have a sensing range of 0-2 bars. The sensors can be of the SMD 3000 series type 3SC-0500-5212 from Merit Sensor Systems.

Motor Controller(s) 62

One or more motors can be connected to the control assembly 10. The operation of these motors is controlled by means of a respective motor controller. In a preferred embodiment, this motor controller consists of 5 H-bridge with current measurement and rotation sensing. The control options are forward, backward, or break. The control is either ON or OFF, i.e., no speed control is implemented. Alternatively, speed control can be implemented, such as by means of a pulse width modulated (PWM) signal.

In order to conserve power, a select signal to each motor's current feedback needs to be activated before any measurements can be done.

The current through the motor is measured in order to differentiate four states:

Normal running operation
Motor stall
Motor short-circuit/open circuit
Slipping of magnetic clutch Different mechanics and motors will have different thresholds for the states. This will be evaluated by software.

The rotation of the motors will be monitored either by an internal encoder in the motor or by external sensors/encoders. The sensing of the movement can be done with a low power Hall element, for example Allegro A139X series, in combination with a comparator that sets the sensitivity or by optical encoders depending on the mechanics. There are two sensors for each motor to be able to determine both speed and direction. End switches can optionally be provided.

Depending on the mechanics and the motors different rotation sensing methods can be used. Exact trip points and hysteresis are application dependent. It should be noted that the mentioned sensors are merely examples and that more types can be added.

Sensing on outgoing axle can be used when there is no encoder on the motor. The rotation sensing can be done with two Hall-effect sensors, such as A1391SE sensors from Allegro MicroSystems, Inc. By using two sensors per motor both direction and speed can be determined. The phase between the detectors shall be 90 degrees, which is set by the mechanical mounting of the devices.

Alternatively, a reflex detector can be used for rotation sensing.

In yet an alternative embodiment, an integrated encoder in the motor can be used for rotation determination.

Stimuli Generator(s) 64

The control assembly can be adapted to control the operation of an implanted medical device in the form of one or more electrodes used to electrically stimulate an organ in the patient's body, such as the corpora cavernosa or crura or the prolongations thereof of a male patient's penile tissue, the colon, rectum, or anus or the prolongation thereof, the urine bladder, the urethra or the prolongation thereof, or any other bodily lumen which requires electrical stimulation under control of the patient or a doctor.

The stimuli generators 64 are designed around a high speed, high current output operational amplifiers, such as the AD825 from Analog Devices, Inc. Each output has a dc current blocking capacitor. A DC servo prevents the capacitor to charge due to offset current errors In one embodiment, the implanted medical device contains 4+4 electrodes to which a constant current pulse generator is connected. The current generator can be connected to two or several electrodes simultaneously.

The current pulses always consist of one positive current pulse and one negative current pulse in any order. The stimuli pulses are configurable regarding current amplitude; pulse widths, number of pulses in a pulse train and pulse frequency. The control assembly 10 ensures that the pulses are charged balanced.

The software of the computer 112 is adapted to write configuration parameters to the control assembly 10 and to start and stop stimulation with those parameters. The stimulation can "move" between different electrodes to e.g. create an artificial peristalsis.

In a preferred embodiment, the stimuli amplitude is be up to 20 mA with +/−14V available.

Capacitor Measurement Device 66

One or more capacitance measuring inputs are provided for determination of a physical or mechanical position. The input has a working range of 5-100 pF.

Motion Sensor 68

The motion sensor is a piezo polymer strip that generates a charge/voltage during movement of an intestine. Each motion sensor is adjusted depending of the application in order to apply an appropriate gain.

Injection Port 70

Figure 8:
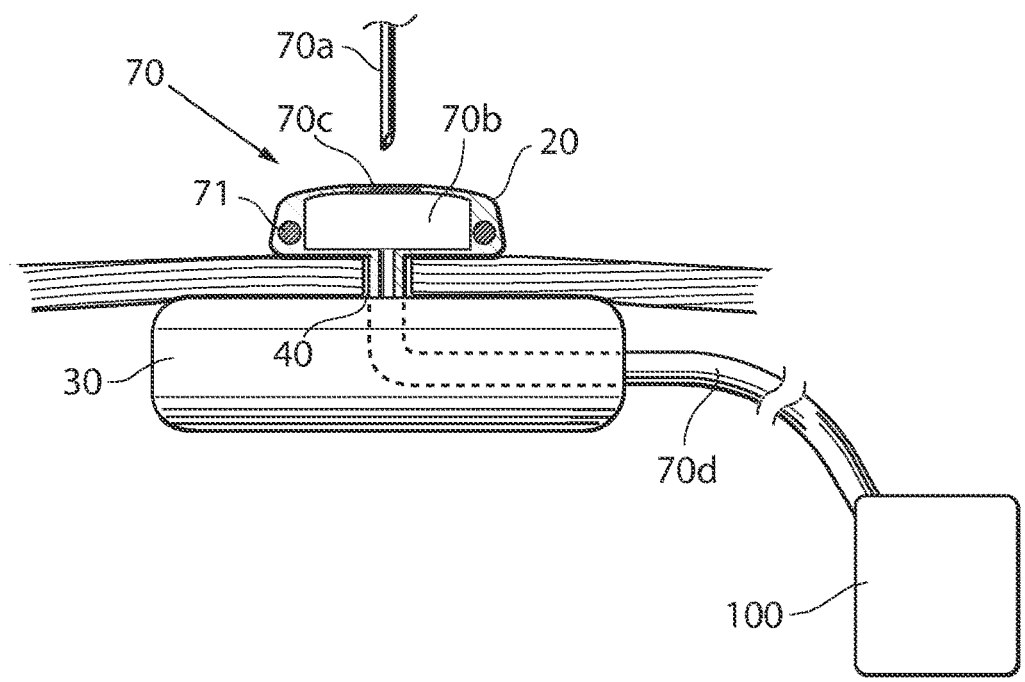
FIG. 8 is a side view of an alternative embodiment of an implanted assembly according to the invention comprising an injection port.

In an alternative embodiment, shown in FIG. 8, the first unit 20 comprises an injection port 70 adapted to receive an injection needle 70a. The injection port comprises a reservoir 70b with a silicone septum 70c. Fluid is added to or removed from the interior reservoir of the first unit 20 by inserting a Huber needle percutaneously into the septum. Although the septum 70c is made of silicone, the means of the injection port for receiving a needle includes any structure configured to self seal after puncture with a non-coring needle.

Optionally, the first unit 20 comprises a magnetic arrangement 71 used as a means for detecting the position of the control assembly 10, which is particularly convenient in the case of an injection port, since a patient or doctor must be able to locate the septum in order to perform accurate puncturing thereof. The magnetic arrangement may include an arrangement as that disclosed in the international publication WO2004/030536(A1), incorporated herein by reference.

A tube or hose 70d is connected to the reservoir 70b and is adapted to be connected to an implanted medical device 100, such as a hydraulically operated constriction device provided about and engaging a bodily organ of the patient, such as the corpora cavernosa or crura or the prolongations thereof of a male patient's penile tissue, the colon, rectum, or anus or the prolongation thereof, the urine bladder, the urethra or the prolongation thereof, or any other bodily lumen which requires partial or full restriction under control of the patient or a doctor. The medical device could also be an adjustable prosthesis device implantable in the corpora cavernosa or other parts of a male impotent patient's penile tissue.

In this embodiment, the tube 70d is provided in the hollow interconnecting device 40 and through the second unit 30.

Pump(s) 72

Figure 9:
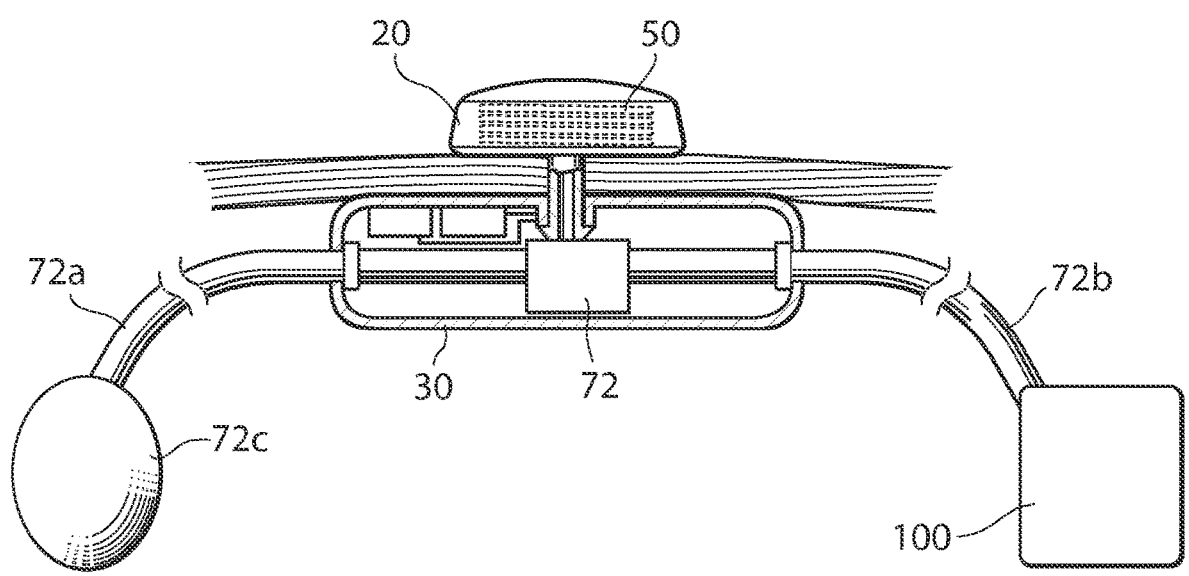
FIG. 9 is a side view of yet an alternative embodiment of an implanted assembly according to the invention comprising a pump.

One or more pumps 72 can be provided in the control assembly 10. Thus, in yet an alternative embodiment of the control assembly 10, shown in FIG. 9, the second unit 30 comprises a pump 72. The pump may be controlled by means of an electronic device in the form of an MCU 52 and associated parts, i.e., transceiver with antenna, charge control unit connected to an energy transfer coil 50 provided in the first unit 20 etc., as have been described above with reference to FIG. 7. The pump is energized through a battery, preferably a rechargeable battery. Alternatively, the pump is energized directly from the energizer 110.

The pump is connected to a first fluid hose 72a and a second fluid hose 72b. These hoses are connectable to reservoirs in the body of the patient and the pump is thus adapted to pump fluid from one part of the patient's body to another part of the patient's body. As an example, in FIG. 9 the first fluid hose 72a is connected to a balancing reservoir 72c. This balancing reservoir 72c is preferably made in the shape of a soft pouch placed in proximity to the second unit 30. It could also be placed directly on a face of or within the second unit. The second fluid hose 72b is connected to an implanted medical device 100, such as a hydraulically operated constriction device provided about and engaging a bodily organ of the patient, such as the corpora cavernosa or crura or the prolongations thereof of a male patient's penile tissue, the colon, rectum, or anus or the prolongation thereof, the urine bladder, the urethra or the prolongation thereof, or any other bodily lumen which requires partial or full restriction under control of the patient or a doctor. The medical device could also be an adjustable prosthesis device implantable in the corpora cavernosa or other parts of a male impotent patient's penile tissue.

Different systems comprising a control assembly 10 will now be described.

FIG. 10 illustrates a system for treating a disease comprising an implanted medical device 100 placed in the abdomen of a patient. An implanted energy-transforming device 1002, corresponding to the control assembly 10, is adapted to supply energy consuming components of the implanted medical device with energy via a power supply line 1003. An external energy-transmission device 1004, corresponding to the energizer 110, for non-invasively energizing the implanted medical device 100 transmits energy by at least one wireless energy signal. The implanted energy-transforming device 1002 transforms energy from the wireless energy signal into electric energy which is supplied via the power supply line 1003.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted medical device 100 is operable in response to the energy of the second form. The energy-transforming device 1002 may directly power the implanted medical device with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the implanted medical device, as the wireless energy is being transmitted by the energy-transmission device 1004. Where the system comprises an operation device for operating the implanted medical device, as will be described below, the wireless energy transmitted by the energy-transmission device 1004 may be used to directly power the operation device to create kinetic energy for the operation of the implanted medical device.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the implanted medical device comprises electric components that are energized with electrical energy. Other implantable electric components of the system may be at least one voltage level guard or at least one constant current guard connected with the electric components of the implanted medical device.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the implanted medical device. Alternatively, the energy-transmission device is controlled from outside the patient's body to release non-magnetic wireless energy, and the released non-magnetic wireless energy is used for operating the implanted medical device.

The external energy-transmission device 1004 also includes a wireless remote control having an external signal transmitter for transmitting a wireless control signal for non-invasively controlling the implanted medical device. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 11 illustrates the system of FIG. 10 in the form of a more generalized block diagram showing the implanted medical device 100, the energy-transforming device 1002 powering the implanted medical device 100 via power supply line 1003, and the external energy-transmission device 1004, The patient's skin 1005, generally shown by a vertical line, separates the interior of the patient to the right of the line from the exterior to the left of the line.

FIG. 12 shows an embodiment of the invention identical to that of FIG. 11, except that a reversing device in the form of an electric switch 1006 operable for example by polarized energy also is implanted in the patient for reversing the implanted medical device 100. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the implanted medical device 100.

FIG. 13 shows an embodiment of the invention identical to that of FIG. 11, except that an operation device 1007 implanted in the patient for operating the implanted medical device 100 is provided between the implanted energy-transforming device 1002 and the implanted medical device 100. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 14 shows an embodiment of the invention identical to that of FIG. 11, except that it also comprises an operation device is in the form of an assembly 1008 including a motor/pump unit 1009 and a fluid reservoir 1010 is implanted in the patient. In this case the implanted medical device 100 is hydraulically operated, i.e. hydraulic fluid is pumped by the motor/pump unit 1009 from the fluid reservoir 1010 through a conduit 1011 to the implanted medical device 100 to operate the implanted medical device, and hydraulic fluid is pumped by the motor/pump unit 1009 back from the implanted medical device 100 to the fluid reservoir 1010 to return the implanted medical device to a starting position. The implanted energy-transforming device 1002 transforms wireless energy into a current, for example a polarized current, for powering the motor/pump unit 1009 via an electric power supply line 1012.

Instead of a hydraulically operated medical device 100, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 15:
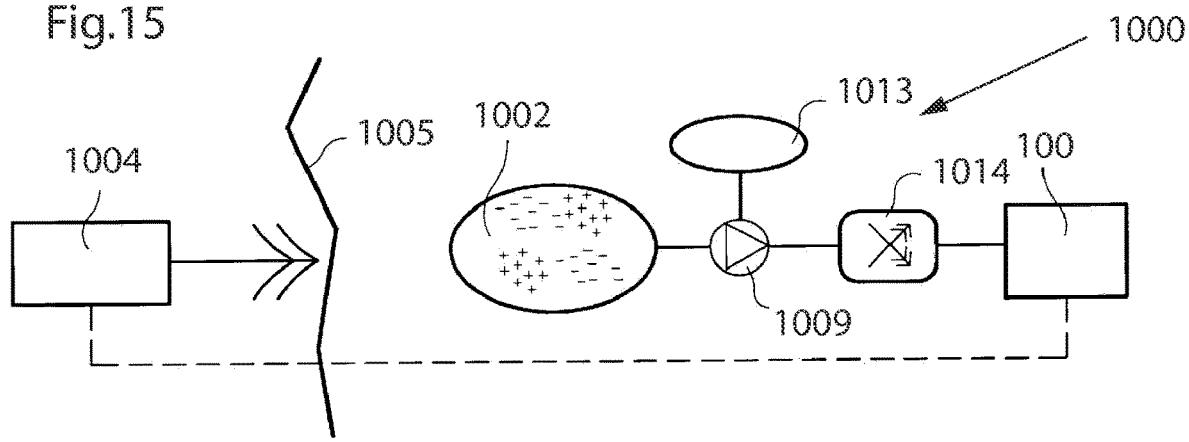

FIG. 15 shows an embodiment of the invention comprising the external energy-transmission device 1004 with its wireless remote control, the medical device 100, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the medical device 100. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the implanted medical device 100 to operate the implanted medical device, and another opposite direction in which the fluid is pumped by the motor/pump unit 1009 back from the implanted medical device 100 to the hydraulic fluid reservoir 1013 to return the implanted medical device to a starting position.

Figure 16:
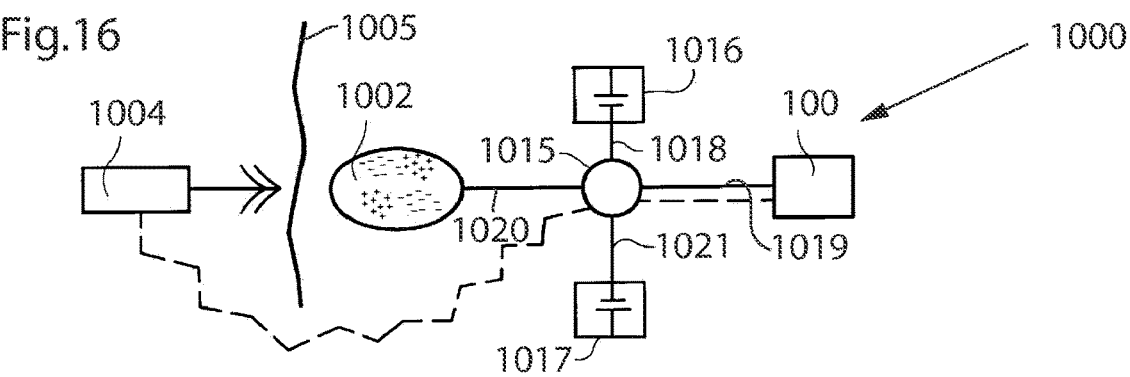

FIG. 16 shows an embodiment of the invention comprising the external energy-transmission device 1004 with its wireless remote control, the medical device 100, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the medical device 100. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the medical device 100.

The internal control unit is preferably programmable from outside the patient's body.

In a preferred embodiment, the internal control unit is programmed to regulate the implanted medical device 100 according to a pre-programmed time-schedule or to input from any sensor sensing any possible physical parameter of the patient or any functional parameter of the system.

In accordance with an alternative, the capacitor 1017 in the embodiment of FIG. 16 may be omitted. In accordance with another alternative, the accumulator 1016 in this embodiment may be omitted.

Figure 17:
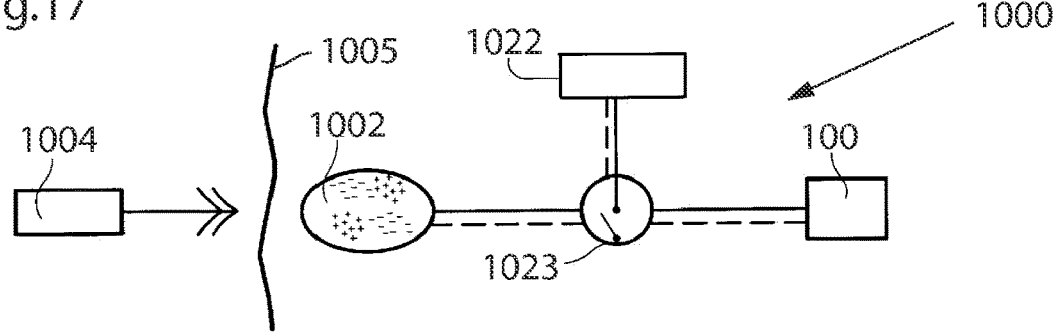

FIG. 17 shows an embodiment of the invention identical to that of FIG. 11, except that a battery 1022 for supplying energy for the operation of the implanted medical device 100 and an electric switch 1023 for switching the operation of the implanted medical device 100 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the medical device 100.

Figure 18:
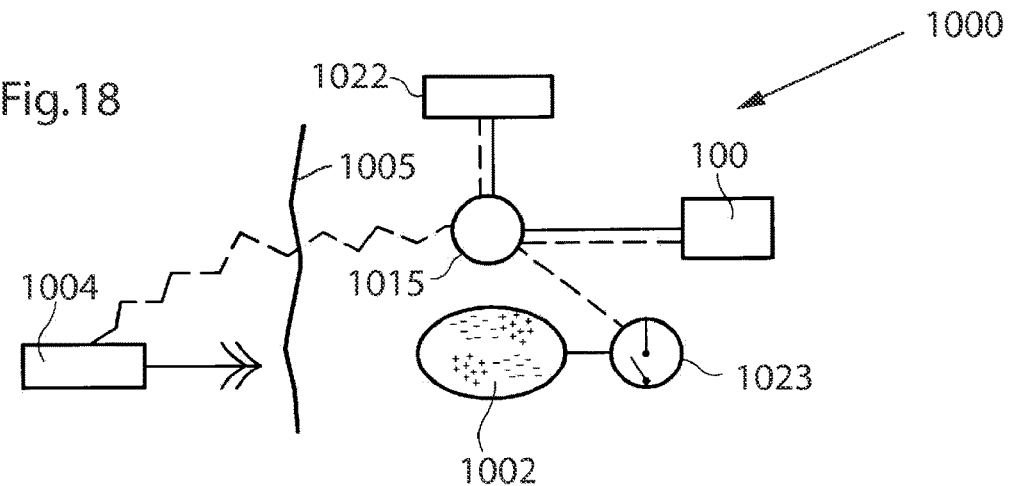

FIG. 18 shows an embodiment of the invention identical to that of FIG. 17, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the medical device 100.

Figure 19:
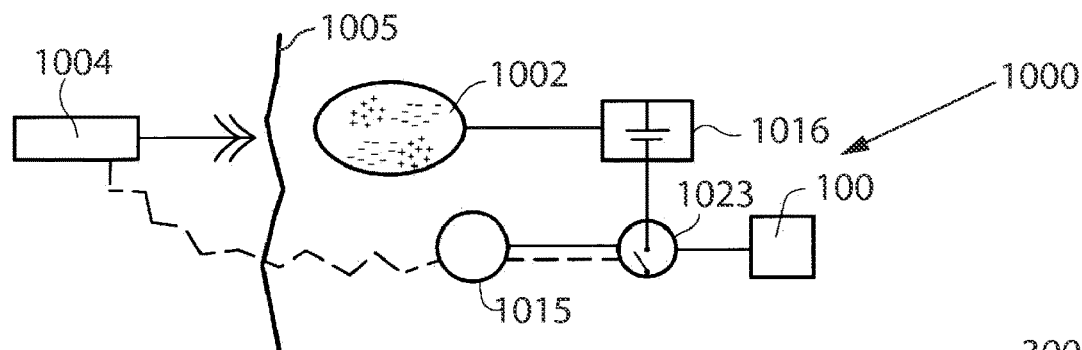

FIG. 19 shows an embodiment of the invention identical to that of FIG. 18, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the medical device 100. The accumulator may be combined with or replaced by a capacitor.

Figure 20:
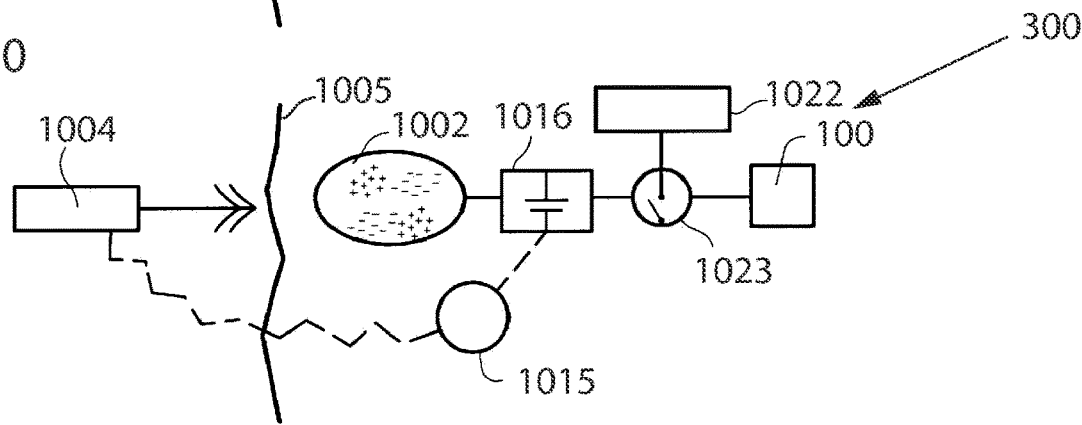

FIG. 20 shows an embodiment of the invention identical to that of FIG. 19, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the medical device 100.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the medical device 100.

It should be understood that the electric switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 21:
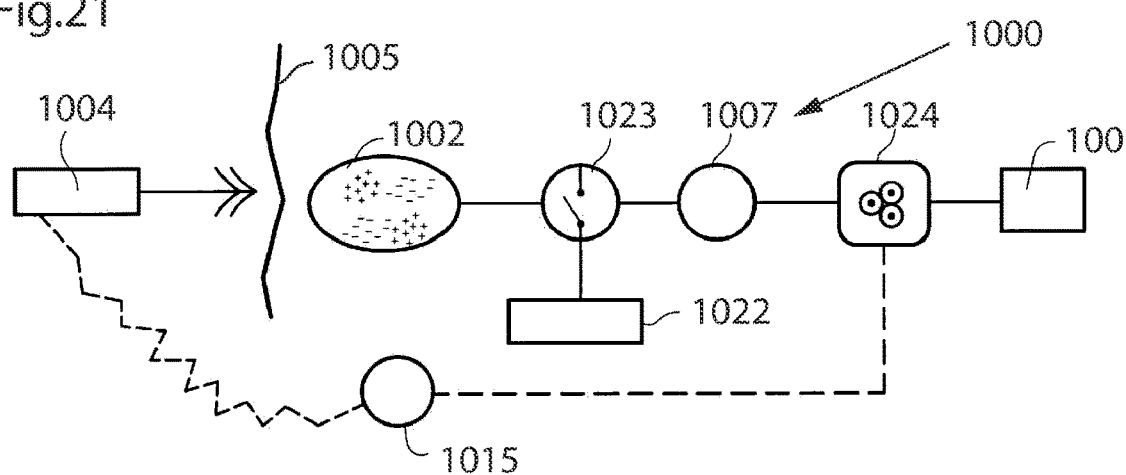

FIG. 21 shows an embodiment of the invention identical to that of FIG. 17, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the implanted medical device 100 (mechanically operated). Even simpler is to switch the direction of the motor electronically. The gear box interpreted in its broadest embodiment may stand for a servo arrangement saving force for the operation device in favor of longer stroke to act.

Figure 22:
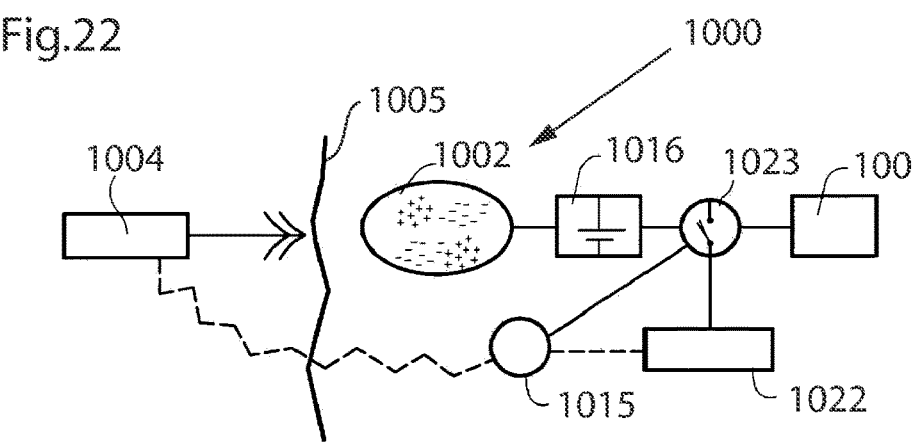

FIG. 22 shows an embodiment of the invention identical to that of FIG. 21 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the medical device 100.

Figure 23:
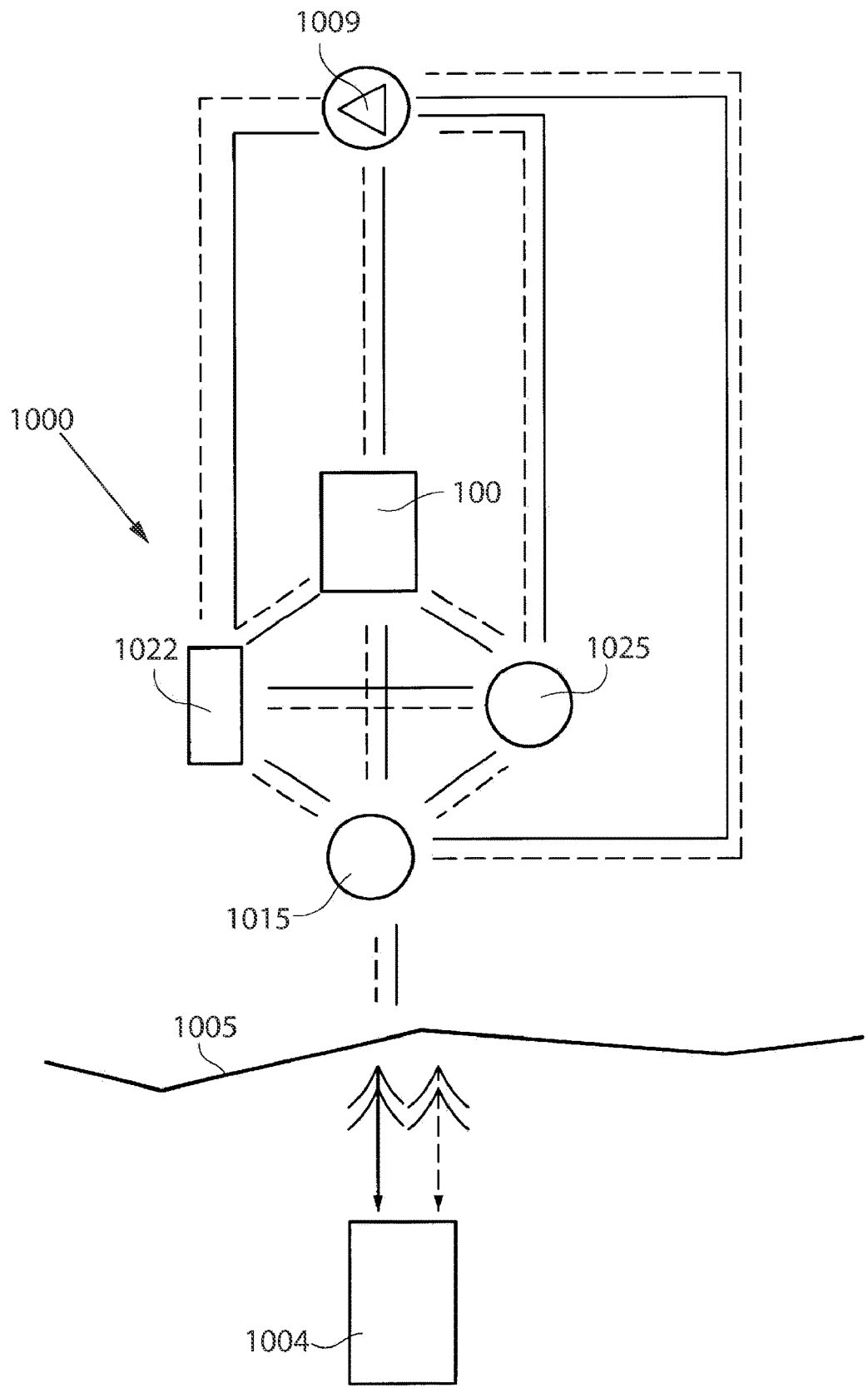

FIG. 23 schematically shows conceivable combinations of implanted components of the system for achieving various communication options. Basically, there are the medical device 100, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the system.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor.

Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the implanted medical device 100 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the implanted medical device 100 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

Figure 24:
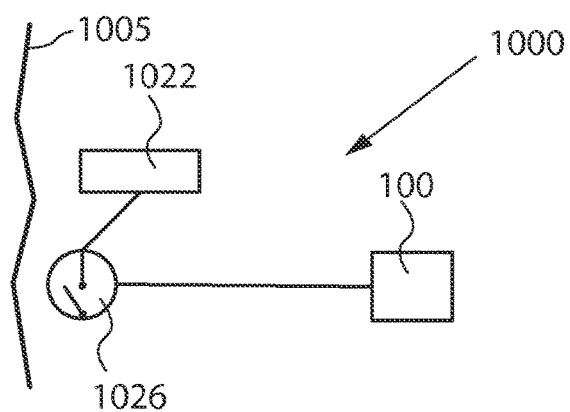

FIG. 24 shows an alternative embodiment wherein the implanted medical device 100 is regulated from outside the patient's body. The system 1000 comprises a battery 1022 connected to the implanted medical device 100 via a subcutaneous electric switch 1026. Thus, the regulation of the implanted medical device 100 is performed non-invasively by manually pressing the subcutaneous switch, whereby the operation of the implanted medical device 100 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 25:
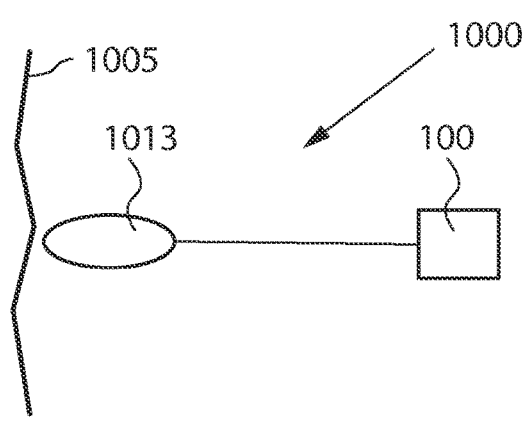

FIG. 25 shows an alternative embodiment, wherein the system 1000 comprises a hydraulic fluid reservoir 1013 hydraulically connected to the implanted medical device. Non-invasive regulation is performed by manually pressing the hydraulic reservoir connected to the implanted medical device.

The system may include an external data communicator and an implantable internal data communicator communicating with the external data communicator. The internal communicator feeds data related to the implanted medical device or the patient to the external data communicator and/or the external data communicator feeds data to the internal data communicator.

Figure 26:
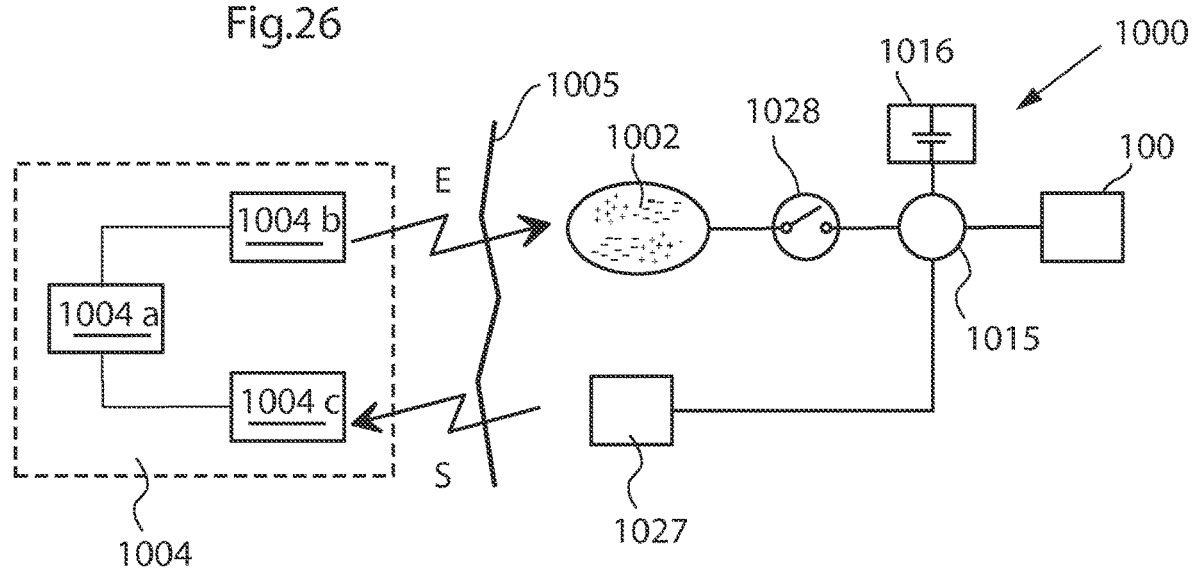
FIG. 26 is a schematic block diagram illustrating an arrangement for supplying an accurate amount of energy used for the operation of the implanted assembly shown in FIG. 1.

FIG. 26 schematically illustrates an arrangement of the system that is capable of sending information from inside the patient's body to the outside thereof to give feedback information related to at least one functional parameter of the implanted medical device or system, or related to a physical parameter of the patient, in order to supply an accurate amount of energy to an implanted internal energy receiver 1002 connected to implanted energy consuming components of the medical device 100. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the implanted medical device 100 via a switch 1026. An energy balance is determined between the energy received by the internal energy receiver 1002 and the energy used for the medical device 100, and the transmission of wireless energy is then controlled based on the determined energy balance. The energy balance thus provides an accurate indication of the correct amount of energy needed, which is sufficient to operate the implanted medical device 100 properly, but without causing undue temperature rise.

In FIG. 26 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the implanted medical device, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the implanted medical device.

The term "energy used" is then understood to include also energy stored by implanted components of the system. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the medical device 100. The internal control unit 1015 may thus be arranged to receive various measurements obtained by suitable sensors or the like, not shown, measuring certain characteristics of the medical device 100, somehow reflecting the required amount of energy needed for proper operation of the medical device 100. Moreover, the current condition of the patient may also be detected by means of suitable measuring devices or sensors, in order to provide parameters reflecting the patient's condition. Hence, such characteristics and/or parameters may be related to the current state of the medical device 100, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the internal control unit 1015 for accumulating received energy for later use by the medical device 100. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the medical device 100, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the medical device 100, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004*b*, thus integrating the above-described function of the internal control unit 1015 in the external control unit 1004*b*. In that case, the internal control unit 1015 can be omitted and the sensor measurements are supplied directly to the internal signal transmitter 1027 which sends the measurements over to the external signal receiver 1004*c* and the external control unit 1004*b*. The energy balance and the currently required amount of energy can then be determined by the external control unit 1004*b* based on those sensor measurements.

Hence, the present solution according to the arrangement of FIG. 26 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the implanted medical device. The system may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the implanted medical device.

The internal signal transmitter 1027 and the external signal receiver 1004*c* may be implemented as separate units using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 26, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 26 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 27:
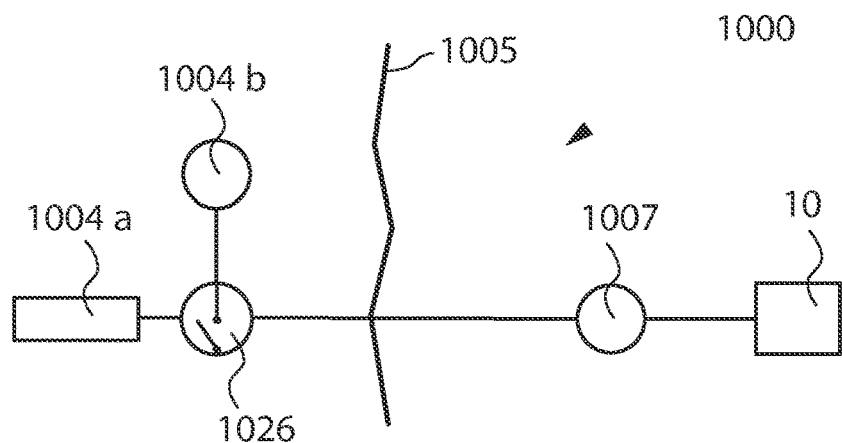
FIG. 27 schematically shows an embodiment of the system, in which the implanted assembly is operated with wire bound energy.

With reference to FIG. 27, although wireless transfer of energy for operating the implanted medical device has been described above to enable non-invasive operation, it will be appreciated that the implanted medical device can be operated with wire bound energy as well. Such an example is shown in FIG. 27, wherein an external switch 1026 is interconnected between the external energy source 1004*a* and an operation device, such as an electric motor 1007 operating the medical device 100. An external control unit

1004*b* controls the operation of the external switch 1026 to effect proper operation of the medical device 100.

Figure 28:
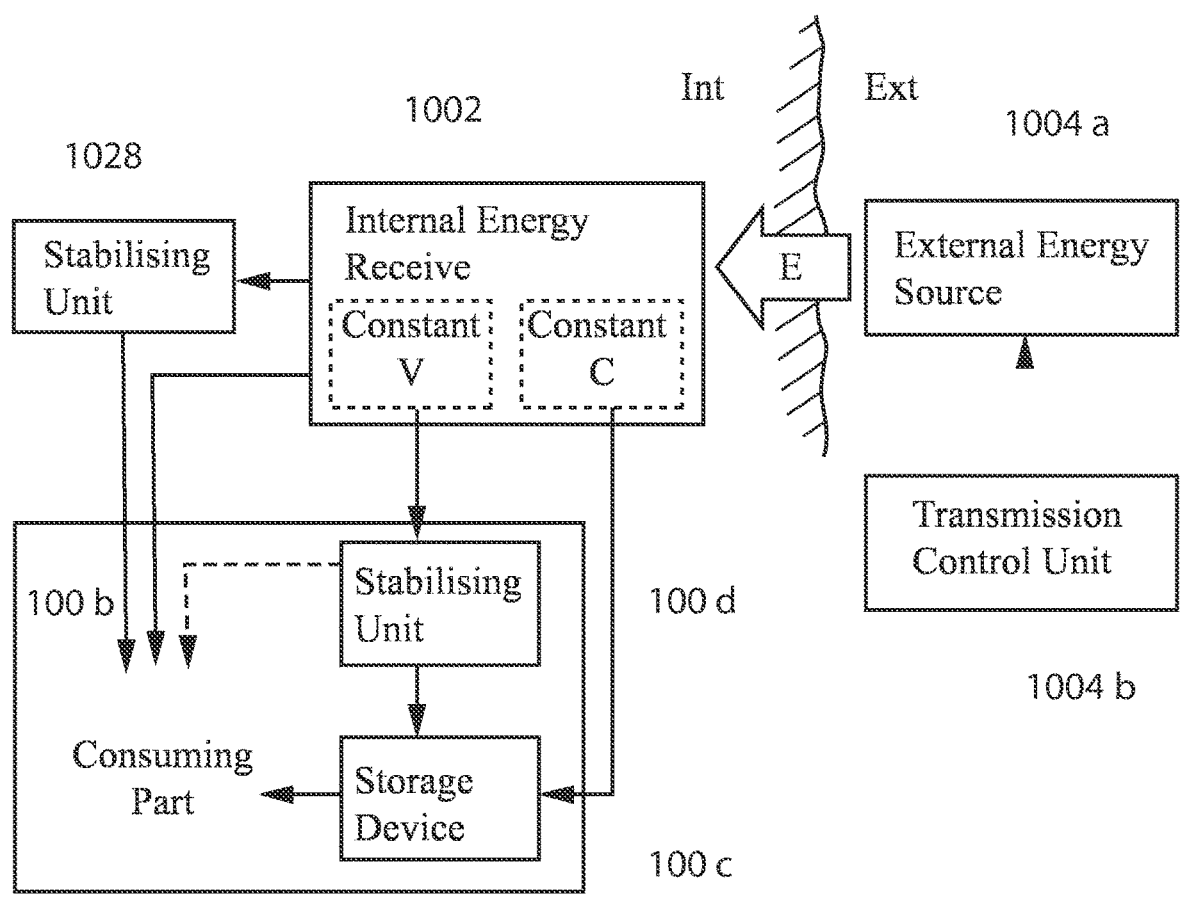
FIG. 28 is a more detailed block diagram of an arrangement for controlling the transmission of wireless energy used for the operation of the implanted assembly shown in FIG. 1.

FIG. 28 illustrates different embodiments for how received energy can be supplied to and used by the medical device 100. Similar to the example of FIG. 26, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the medical device 100. The internal energy receiver 1002 may further comprise a constant current circuit, indicated as a dashed box "constant C" in the figure, for supplying energy at constant current to the medical device 100.

The implanted medical device 100 comprises an energy consuming part 100*b*, which may be a motor, pump, restriction device, or any other medical appliance that requires energy for its electrical operation. The implanted medical device 100 may further comprise an energy storage device 100*c* for storing energy supplied from the internal energy receiver 1002. Thus, the supplied energy may be directly consumed by the energy consuming part 100*b*, or stored by the energy storage device 100*c*, or the supplied energy may be partly consumed and partly stored. The implanted medical device 100 may further comprise an energy stabilizing unit 100*d* for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the medical device 100, before being consumed and/or stored by the medical device 100. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 26 and FIG. 28 illustrate some possible but non-limiting implementation options regarding how the various shown functional components and elements can be arranged and connected to each other. However, the skilled person will readily appreciate that many variations and modifications can be made within the scope of the present invention.

Figure 29:
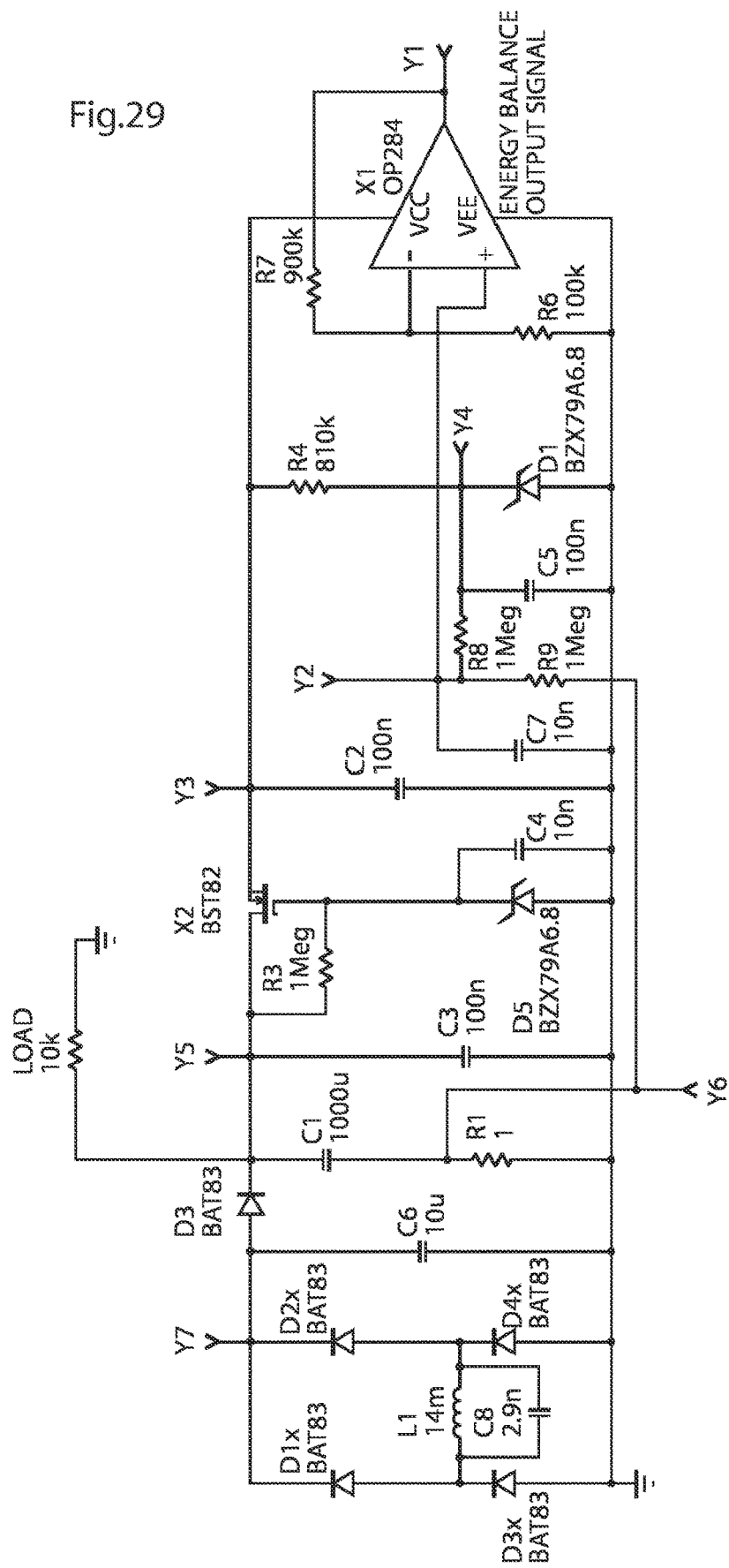
FIG. 29 is a circuit for the arrangement shown in FIG. 19, according to a possible implementation example.

FIG. 29 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the system, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 29 shows a circuit implementation for a system that transfers energy to the implanted energy components of the system of the present invention from outside of the patient's body using inductive energy transfer. An inductive energy transfer system typically uses an external transmitting coil and an internal receiving coil. The receiving coil, L1, is included in the schematic FIG. 12; the transmitting parts of the system are excluded.

The implementation of the general concept of energy balance and the way the information is transmitted to the external energy transmitter can of course be implemented in numerous different ways. The schematic FIG. 29 and the above described method of evaluating and transmitting the information should only be regarded as examples of how to implement the control system.

Circuit Details

In FIG. 29 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 12 could be incorporated in any of the embodiments of FIGS. 15-21, the hydraulic valve shifting device 1014 of FIG. 15 could be incorporated in the embodiment of FIG. 14, and the gear box 1024 could be incorporated in the embodiment of FIG. 13. Please observe that the switch simply could mean any electronic circuit or component.

The embodiments described in connection with FIGS. 26, 28 and 29 identify a method and a system for controlling transmission of wireless energy to implanted energy consuming components of an electrically operable system. Such a method and system will be defined in general terms in the following.

A method is thus provided for controlling transmission of wireless energy supplied to implanted energy consuming components of a system as described above. The wireless energy E is transmitted from an external energy source located outside the patient and is received by an internal energy receiver located inside the patient, the internal energy receiver being connected to the implanted energy consuming components of the system for directly or indirectly supplying received energy thereto. An energy balance is determined between the energy received by the internal energy receiver and the energy used for the system. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an implanted medical device as described above is thus also provided for controlling transmission of wireless energy supplied to implanted energy consuming components of the system. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the system for directly or indirectly supplying received energy thereto. The system further comprises a determination device adapted to determine an energy balance between the energy received by the internal energy receiver and the energy used for the implantable energy consuming components of the system, wherein the control device controls the transmission of wireless energy from the external energy-transmission device, based on the energy balance determined by the determination device.

Further, the system may comprise any of the following:

- A primary coil in the external energy source adapted to transmit the wireless energy inductively to a secondary coil in the internal energy receiver.
- A determination device adapted to detect a change in the energy balance, wherein the control device controls the transmission of wireless energy based on the detected energy balance change
- A determination device adapted to detect a difference between energy received by the internal energy receiver and energy used for the implantable energy consuming components of the system, wherein the control device controls the transmission of wireless energy based on the detected energy difference.
- A control device controlling the external energy-transmission device to decrease the amount of transmitted wireless energy if the detected energy balance change implies that the energy balance is increasing, or vice versa, wherein the decrease/increase of energy transmission corresponds to a detected change rate.
- A control device controlling the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
- An implanted medical device wherein the energy used for the implanted medical device is consumed to operate the implanted medical device, and/or stored in at least one energy storage device of the system.
- An implanted medical device where electrical and/or physical parameters of the implanted medical device and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

An implanted medical device wherein, wherein a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

An implanted medical device wherein the derivative is determined over time of a measured electrical parameter related to the amount of consumed and/or stored energy, the determination device determines the derivative for a monitored voltage and/or current related to the energy balance.

An energy-transmission device comprising a coil placed externally to the human body, and an electric circuit provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

An electric circuit adapted to deliver the electrical pulses to remain unchanged except varying the first and/or second time intervals.

An electric circuit having a time constant and being adapted to vary the first and second time intervals only in the range of the first time constant, so that when the lengths of the first and/or second time intervals are varied, the transmitted power over the coil is varied.

An electric circuit adapted to deliver the electrical pulses to be varied by only varying the lengths of first time intervals between successive leading and trailing edges of the electrical pulses.

An electric circuit adapted to supply a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

An electric circuit adapted to provide the electrical pulses as pulses having a substantially constant height and/or amplitude and/or intensity and/or voltage and/or current and/or frequency.

An electric circuit having a time constant, and being adapted to vary the first and second time intervals only in the range of the first time constant, so that when the lengths of the first and/or second time intervals are varied, the transmitted power across the first coil are varied.

An electric circuit adapted to provide the electrical pulses varying the lengths of the first and/or the second time intervals only within a range that includes the first time constant or that is located relatively close to the first time constant, compared to the magnitude of the first time constant.

FIGS. 30-33 show in more detail block diagrams of four different ways of hydraulically or pneumatically powering an implanted medical device according to the invention.

Figure 30:
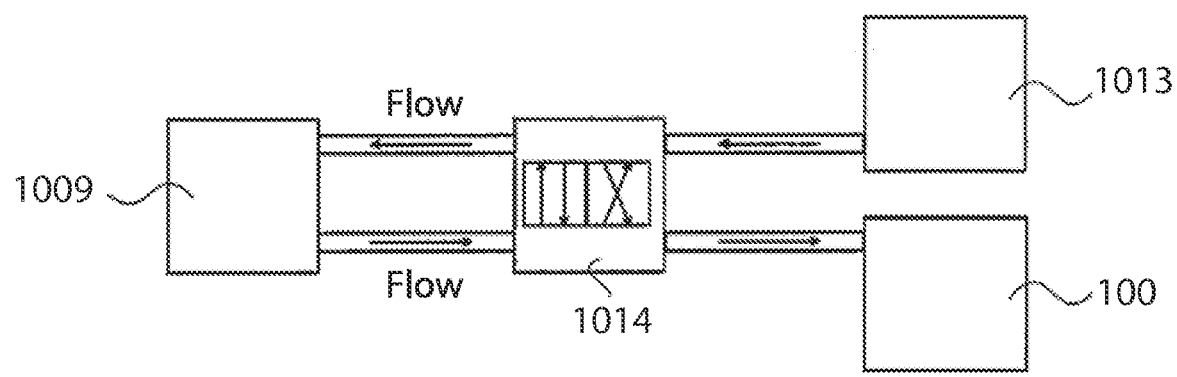

FIG. 30 shows a system as described above with. The system comprises an implanted medical device 100 and further a separate regulation reservoir 1013, a one way pump 1009 and an alternate valve 1014.

Figure 31:
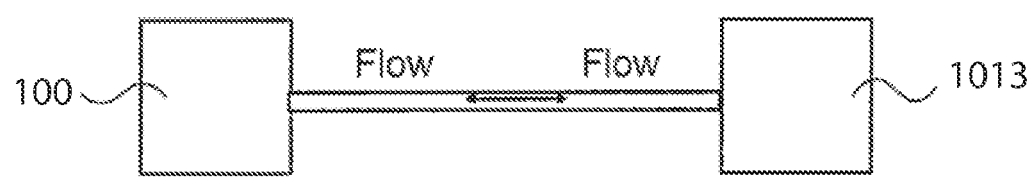

FIG. 31 shows the implanted medical device 100 and a fluid reservoir 1013. By moving the wall of the regulation reservoir or changing the size of the same in any other different way, the adjustment of the implanted medical device may be performed without any valve, just free passage of fluid any time by moving the reservoir wall.

Figure 32:
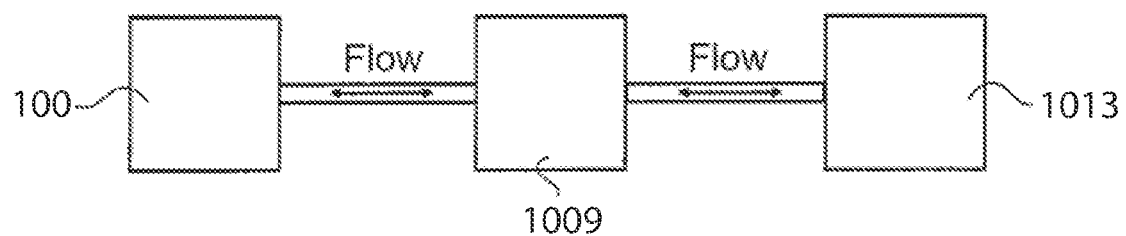

FIG. 32 shows the medical device 100, a two way pump 1009 and the regulation reservoir 1013.

Figure 33:
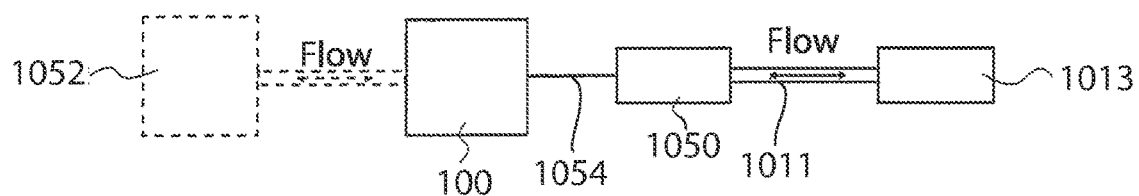

FIG. 33 shows a block diagram of a reversed servo system with a first closed system controlling a second closed system. The servo system comprises a regulation reservoir 1013 and a servo reservoir 1050. The servo reservoir 1050 mechanically controls an implanted medical device 100 via a mechanical interconnection 1054. The implanted medical device has an expandable/contactable cavity. This cavity is preferably expanded or contracted by supplying hydraulic fluid from the larger adjustable reservoir 1052 in fluid connection with the medical device 100. Alternatively, the cavity contains compressible gas, which can be compressed and expanded under the control of the servo reservoir 1050.

The servo reservoir 1050 can also be part of the implanted medical device itself.

Figure 34:
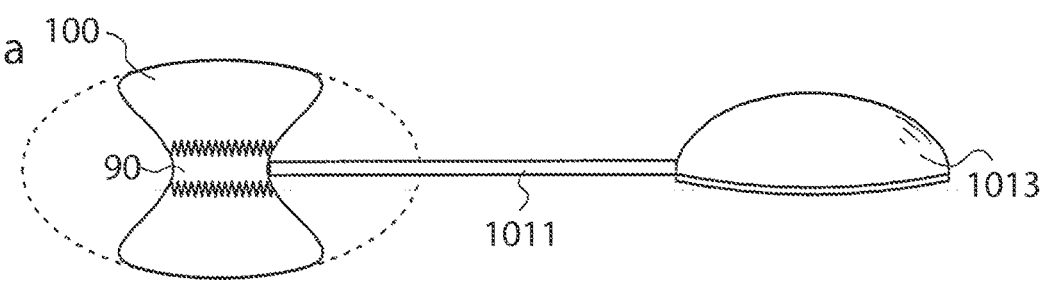
Figure 34:
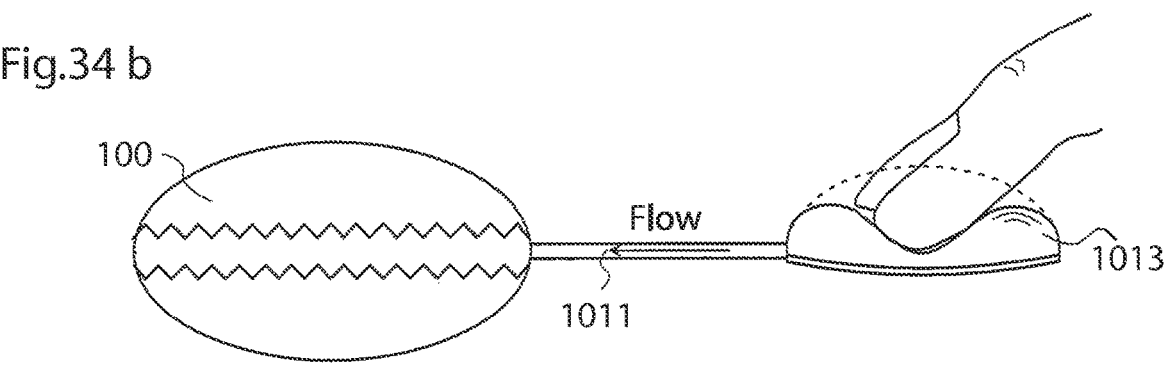
Figure 34:
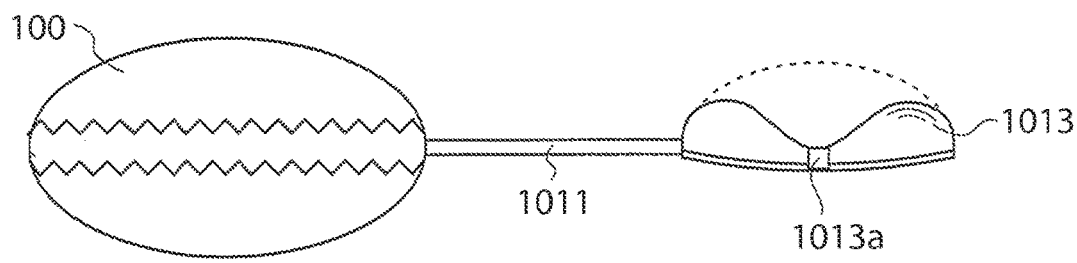
Figure 35:
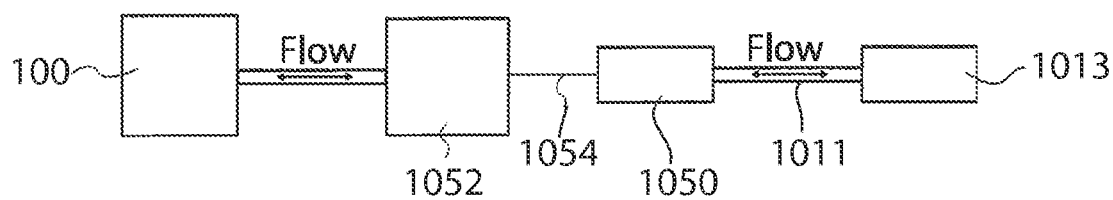

In one embodiment, the regulation reservoir is placed subcutaneous under the patient's skin and is operated by pushing the outer surface thereof by means of a finger. This system is illustrated in FIGS. 34a-c. In FIG. 34a, a flexible subcutaneous regulation reservoir 1013 is shown connected to a bulge shaped servo reservoir 1050 by means of a conduit 1011. This bellow shaped servo reservoir 1050 is comprised in a flexible medical device 100. In the state shown in FIG. 34a, the servo reservoir 1050 contains a minimum of fluid and most fluid is found in the regulation reservoir 1013. Due to the mechanical interconnection between the servo reservoir 1050 and the medical device 100, the outer shape of the implanted medical device 100 is contracted, i.e., it occupies less than its maximum volume. This maximum volume is shown with dashed lines in the figure.

FIG. 34b shows a state wherein a user, such as the patient in with the medical device is implanted, presses the regulation reservoir 1013 so that fluid contained therein is brought to flow through the conduit 1011 and into the servo reservoir 1050, which, thanks to its bellow shape, expands longitudinally. This expansion in turn expands the implanted medical device 100 so that it occupies its maximum volume, thereby stretching the stomach wall (not shown), which it contacts.

The regulation reservoir 1013 is preferably provided with means 1013a for keeping its shape after compression. This means, which is schematically shown in the figure, will thus keep the implanted medical device 100 in a stretched position also when the user releases the regulation reservoir. In this way, the regulation reservoir essentially operates as an on/off switch for the system.

An alternative embodiment of hydraulic or pneumatic operation will now be described with reference to FIGS. 35 and 36a-c. The block diagram shown in FIG. 35 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted medical device 100 having an expandable/contactable cavity is in turn controlled by the larger adjustable reservoir 1052 by supply of hydraulic fluid from the larger adjustable reservoir 1052 in fluid connection with the medical device 100.

Figure 36:
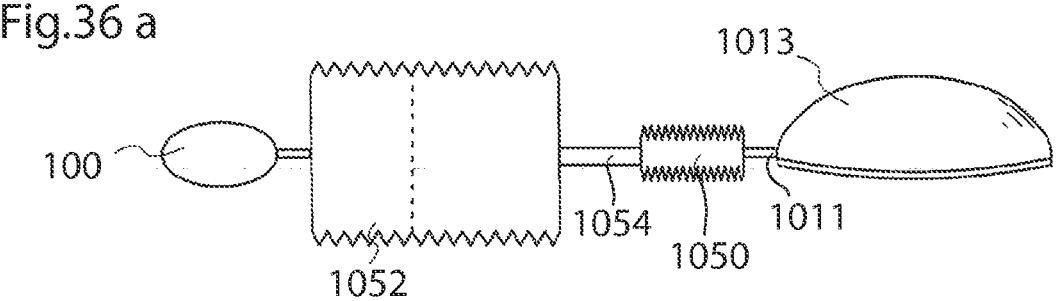
Figure 36:
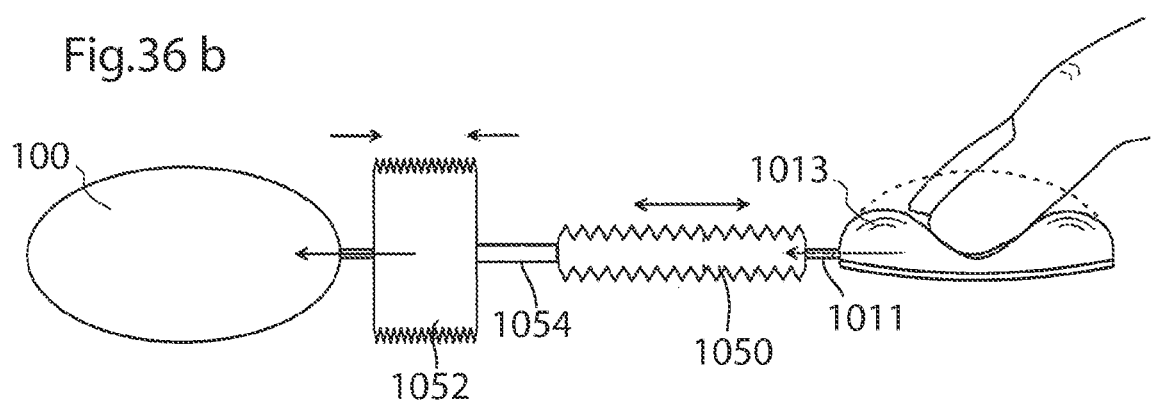
Figure 36:
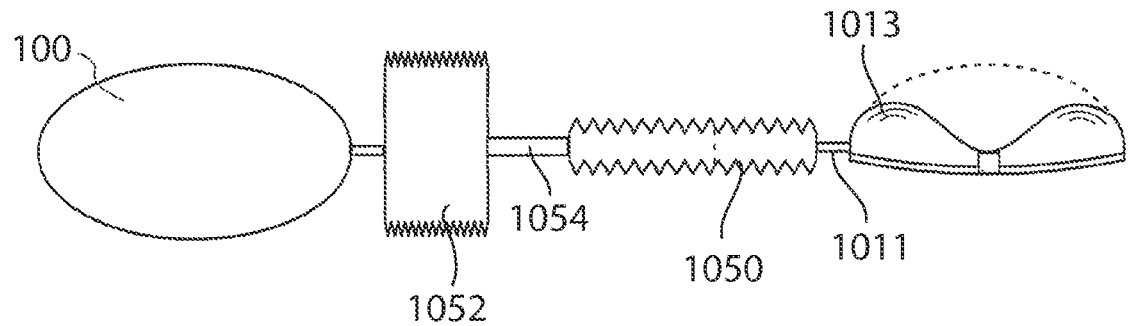

An example of this embodiment will now be described with reference to FIG. 36*a-c*. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 36*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the medical device 100. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the medical device 100. In other words, in this reversed servo, a small volume in the regulation reservoir is compressed with a higher force and this creates a movement of a larger total area with less force per area unit.

Like in the previous embodiment described above with reference to FIGS. 25*a-c*, the regulation reservoir 1013 is preferably provided with means 1013*a* for keeping its shape after compression. This means, which is schematically shown in the figure, will thus keep the implanted medical device 100 in a stretched position also when the user releases the regulation reservoir. In this way, the regulation reservoir essentially operates as an on/off switch for the system.

The control assembly 10 can be placed in the body of a patient by different methods. One method comprises the steps of:
inserting a needle or tube like instrument into the abdomen of the patient's body,
using the needle or tube like instrument to fill the abdomen with gas thereby expanding the abdominal cavity,
placing at least two laparoscopic trocars in the patient's body,
inserting a camera through one of the trocars into the abdomen,
inserting at least one dissecting tool through a trocar and dissecting an area of a body tissue of the patient,
placing a first unit of the control assembly at a first side of the body tissue of the patient,
placing a second unit of the control assembly at a second side of the body tissue of the patient, and
placing an interconnecting device adapted for mechanical interconnection of the first and second units to keep the assembly in place by the body tissue, the interconnecting device having a cross-sectional area which is smaller than the cross-sectional area of the first unit and the second unit in a plane parallel to the extension of the body tissue.

Another method for placing a control assembly 10 in a human or mammal patient comprises the steps of:
cutting the skin of the patient
dissecting an area of a body tissue,
placing a first unit of the control assembly at a first side of the body tissue of the patient,
placing a second unit of the control assembly at a second side of the body tissue of the patient, and
placing an interconnecting device adapted for mechanical interconnection of the first and second units to keep the assembly in place by the body tissue, the interconnecting device having a cross-sectional area which is smaller than the cross-sectional area of the first unit and the second unit in a plane parallel to the extension of the body tissue.

Preferred embodiments of a control assembly according to the invention have been described. A person skilled in the art realizes that these could be varied within the scope of the appended claims. Thus, one or more parts of the embodiment described with reference to FIG. 7 can be omitted without departing from the inventive idea.

The invention claimed is:

1. A control assembly for implantation in a patient, the control assembly comprising:
a first unit adapted for subcutaneous implantation at a first side of a body tissue of said patient,
a second unit adapted for implantation in a body cavity of said patient at a second side of said body tissue opposite of the side at which the first unit is provided, wherein at least one of the first unit and the second unit is adapted to control an implanted powered medical device, and
an interconnecting device adapted for mechanical interconnection of the first unit and the second unit to keep the control assembly in place by the body tissue, the interconnecting device having a cross-sectional area which is smaller than a cross-sectional area of the first unit and the second unit in a plane parallel to an extension of the body tissue,
wherein the first unit and the second unit are adapted to prevent slippage through the body tissue, whereby the control assembly is kept in place with the first unit and the second unit placed on the opposite sides of said body tissue,
wherein the first unit comprises an energy receiver, and
wherein the interconnecting device houses wires electrically interconnecting the first unit and the second unit wherein the wires connect the energy receiver with functional parts provided in the second unit,
wherein the functional parts correspond to parts of the control assembly for electrical or hydraulic operation of the control assembly.

2. The control assembly according to claim 1, wherein the energy receiver is adapted to receive wireless energy.

3. The control assembly according to claim 1, wherein the energy receiver is a coil.

4. The control assembly according to claim 3, wherein the coil is adapted to be used as an antenna.

5. The control assembly according to claim 1, comprising an antenna.

6. The control assembly according to claim 1, comprising an injection port.

7. The control assembly according to claim 1, comprising a pump.

8. The control assembly according to claim 1, comprising a battery.

9. The control assembly according to claim 8, wherein the battery is rechargeable.

10. The control assembly according to claim 1, wherein the first unit comprises a first electronic device.

11. The control assembly according to claim 1, wherein the second unit comprises a second electronic device.

12. The control assembly according to claim 1, wherein said second unit comprises an electrical stimulation device controller.

13. The control assembly according to claim 1, wherein said second unit comprises a motor controller.

14. The control assembly according to claim 1, wherein said second unit comprises a motor.

15. The control assembly according to claim 1, wherein the interconnecting device has circular cross-sectional shape.

16. The control assembly according to claim 1, wherein the interconnecting device is hollow.

17. The control assembly according to claim 1, wherein the body cavity is one of the following:
   a thorax of the patient,
   abdomen of the patient, and
   an artificially created cavity in the body of the patient.

18. The control assembly according to claim 1, wherein the body tissue is one of:
   a muscle tissue of the patient,
   a rectus abdominis of the patient, and
   a bone.

19. The control assembly according to claim 1, comprising a cover covering the first and second unit.

20. The control assembly according to claim 19, wherein the cover is any of the following:
   a resilient cover, and
   a silicone cover.

* * * * *